(12) United States Patent
Assouad

(10) Patent No.: US 12,633,406 B2
(45) Date of Patent: May 19, 2026

(54) SYSTEM AND METHOD FOR ADAPTIVE USER EXPERIENCE CYCLE PROFILING UNDER ANOMALOUS ENVIRONMENTAL RESPIRATORY CONDITIONS

(71) Applicant: SPECTRONIX INC., Gatineau (CA)

(72) Inventor: Patrick Assouad, Ottawa (CA)

(73) Assignee: SPECTRONIX INC., Gatineau (CA)

( * ) Notice: Subject to any disclaimer, the term of this patent is extended or adjusted under 35 U.S.C. 154(b) by 313 days.

(21) Appl. No.: 18/033,327

(22) PCT Filed: Oct. 25, 2021

(86) PCT No.: PCT/CA2021/051499
§ 371 (c)(1),
(2) Date: Apr. 21, 2023

(87) PCT Pub. No.: WO2022/082322
PCT Pub. Date: Apr. 28, 2022

(65) Prior Publication Data
US 2023/0395249 A1 Dec. 7, 2023

Related U.S. Application Data

(60) Provisional application No. 63/125,367, filed on Dec. 14, 2020, provisional application No. 63/105,223, filed on Oct. 24, 2020.

(51) Int. Cl.
*G16H 40/63* (2018.01)
*A61B 5/145* (2006.01)
*B63C 11/02* (2006.01)

(52) U.S. Cl.
CPC ............. *G16H 40/63* (2018.01); *B63C 11/02* (2013.01); *A61B 5/14542* (2013.01); *B63C 2011/021* (2013.01)

(58) Field of Classification Search
CPC ... A61B 5/0075; A61B 5/6803; A61B 5/7275; A61B 5/14542; A61B 5/14551;
(Continued)

(56) References Cited

U.S. PATENT DOCUMENTS

| | | | |
|---|---|---|---|
| 4,775,116 A | 10/1988 | Klein | |
| 5,315,995 A | 5/1994 | Rivers | |

(Continued)

FOREIGN PATENT DOCUMENTS

| | | |
|---|---|---|
| CA | 3077122 | 10/2021 |
| CA | 3115419 | 10/2021 |

(Continued)

OTHER PUBLICATIONS

International Search Report and Written Opinion issued in Application No. PCT/CA2021/051499, 9 pages, dated Jan. 27, 2022.
(Continued)

*Primary Examiner* — John H Le
(74) *Attorney, Agent, or Firm* — Gray Ice Higdon

(57) ABSTRACT
Described are various embodiments of a system and method for adaptive user experience cycle profiling under anomalous environmental respiratory conditions, such as in hyperbaric or hypobaric environments. In one embodiment, the system comprises an environmental sensor operable to monitor a respiratory environment parameter representative of the anomalous environmental respiratory condition that defines the experience cycle; and a physiological sensor operable to concurrently monitor a physiological parameter representative of the user's cumulative physiological response to the anomalous environmental respiratory condition over time during the experience cycle.

21 Claims, 18 Drawing Sheets

(58) Field of Classification Search
CPC ... B63C 11/02; B63C 2011/021; G16H 40/63; G16H 50/30; G16H 15/00
USPC ........................................................ 702/189
See application file for complete search history.

(56) References Cited

U.S. PATENT DOCUMENTS

| | | | |
|---|---|---|---|
| 5,355,882 A | 10/1994 | Ukawa et al. | |
| 5,372,134 A | 12/1994 | Richardson | |
| 5,388,575 A | 2/1995 | Taube | |
| 5,457,284 A | 10/1995 | Ferguson | |
| 6,671,529 B2 | 12/2003 | Claure et al. | |
| 7,127,278 B2 | 10/2006 | Melker et al. | |
| 7,190,999 B2 | 3/2007 | Geheb et al. | |
| 8,712,493 B2 | 4/2014 | Ukawa | |
| 9,014,772 B2 | 4/2015 | Yamaguchi et al. | |
| 9,131,881 B2 | 9/2015 | Diab et al. | |
| 9,579,060 B1 | 2/2017 | Lisy et al. | |
| 9,775,546 B2 | 10/2017 | Diab et al. | |
| 10,531,819 B2 | 1/2020 | Diab et al. | |
| 10,660,551 B2 | 5/2020 | Koyama et al. | |
| 10,674,948 B2 | 6/2020 | Diab et al. | |
| 11,071,480 B2 | 7/2021 | Diab et al. | |
| 12,064,247 B2 * | 8/2024 | Everman .................. A61B 5/18 | |
| 2002/0019587 A1 | 2/2002 | Cheng et al. | |
| 2003/0050541 A1 | 3/2003 | Wuori | |
| 2004/0267325 A1 | 12/2004 | Geheb et al. | |
| 2005/0070778 A1 | 3/2005 | Lackey et al. | |
| 2005/0228246 A1 | 10/2005 | Lee et al. | |
| 2006/0173258 A1 | 8/2006 | Kobayashi et al. | |
| 2007/0213964 A1 | 9/2007 | Goldman | |
| 2008/0139908 A1 | 6/2008 | Kurth | |
| 2008/0171311 A1 | 7/2008 | Centen et al. | |
| 2008/0200775 A1 | 8/2008 | Lynn | |
| 2008/0262327 A1 | 10/2008 | Kato | |
| 2008/0269589 A1 | 10/2008 | Thijs et al. | |
| 2008/0306337 A1 | 12/2008 | Livingston et al. | |
| 2010/0076319 A1 | 3/2010 | Mannheimer et al. | |
| 2011/0218409 A1 | 9/2011 | Kugler et al. | |
| 2011/0245711 A1 | 10/2011 | Katra et al. | |
| 2012/0065486 A1 | 3/2012 | Imran | |
| 2013/0281803 A1 | 10/2013 | Scheele et al. | |
| 2014/0012144 A1 | 1/2014 | Crone | |
| 2014/0100788 A1 | 4/2014 | Heikkinen et al. | |
| 2015/0254414 A1 | 9/2015 | Patel | |
| 2017/0071550 A1 | 3/2017 | Newberry | |
| 2017/0112422 A1 | 4/2017 | Hatch | |
| 2017/0119254 A1 | 5/2017 | Ando et al. | |
| 2017/0224220 A1 | 8/2017 | Tunnell et al. | |
| 2017/0325784 A1 | 11/2017 | Friedrich et al. | |
| 2018/0001980 A1 | 1/2018 | Hulbert | |
| 2018/0207058 A1 | 7/2018 | Xu et al. | |
| 2018/0310822 A1 | 11/2018 | Indorf et al. | |
| 2019/0290194 A1 | 9/2019 | Umekawa et al. | |
| 2020/0310098 A1 | 10/2020 | Ince et al. | |

FOREIGN PATENT DOCUMENTS

| | | |
|---|---|---|
| CN | 1245407 | 2/2000 |
| CN | 1326328 | 12/2001 |
| CN | 103203013 | 7/2013 |
| EP | 1304955 | 5/2003 |
| EP | 2075189 | 7/2009 |
| JP | H05124592 | 5/1993 |
| JP | 1993207993 | 11/2000 |
| JP | 3116252 | 12/2000 |
| JP | 2008534083 | 8/2008 |
| JP | 2009501041 | 1/2009 |
| JP | 2018536516 | 12/2018 |
| JP | 2019502418 | 1/2019 |
| WO | 2007080303 | 7/2007 |
| WO | 2008013506 | 1/2008 |
| WO | 2009022926 | 2/2009 |
| WO | 2010129528 | 11/2010 |
| WO | 2013165887 | 11/2013 |
| WO | 2017078637 | 5/2017 |
| WO | 2019081547 | 5/2019 |
| WO | 2019213783 | 11/2019 |
| WO | 2022082322 | 4/2022 |
| WO | 2022082323 | 4/2022 |

OTHER PUBLICATIONS

U.S. Appl. No. 17/046,704, filed May 10, 2019, Patrick Assouad.

U.S. Appl. No. 63/105,223, filed Oct. 24, 2020, Patrick Assouad.

U.S. Appl. No. 63/125,367, filed Dec. 14, 2020, Patrick Assouad.

Bein et al. Monitoring of cerebral oxygenation with near infrared spectroscopy and tissue oxygen partial pressure during cardiopulmonary resuscitation in pigs. European Journal of Anaesthesiology 2006; 23: 501-509.

Callaway. Cerebral Oximetry and Cardiopulmonary Resuscitation. Journal of the American Heart Association. Jul. 28, 2021. pp. 1-2.

Chien et al. Cerebral Oxygenation During Hypoxia and Resuscitation by Using Near-infrared Spectroscopy in Newborn Piglets. ChinMedAssoc • Feb. 2007 • vol. 70 • No. 2. pp 47-55.

Genbrugge et al. Regional Cerebral Oximetry During Cardiopulmonary Resuscitation: Useful Or Useless? The Journal of Emergency Medicine, vol. 50, No. 1, pp. 198-207, 2016.

Green et al. Cerebral oximetry and its role in adult cardiac, non-cardiac surgeryand resuscitation from cardiac arrest. Anaesthesia 2017, 72 (Suppl. 1), 48-57.

Hanning CD, Alexander-Williams JM. Pulse oximetry: a practical review. BMJ. 1995;311(7001):367-370. doi:10.1136/bmj.311.7001.367.

Hirose et al. Pre-hospital portable monitoring of cerebral regional oxygen saturation (rSO2) in seven patients with out-of-hospital cardiac arrest. BMC Res Notes (2016) 9:428 pp. 1-5.

Ibrahim et al. Cerebral Oximetry as a Real-Time Monitoring Tool to Assess Quality ofIn-Hospital Cardiopulmonary Resuscitation and Post Cardiac Arrest Care. Journal of the American Heart Association. Jul. 28, 2021. pp. 1-5.

Jones, et al., Underwater near-infrared spectroscopy measurements of muscle oxygenation: laboratory validation and preliminary observations in swimmers and triathletes, Journal of Biomedical Optics 19(12), Dec. 2014.

Larsson A., Uusijärvi J., Eksborg S., "Tissue oxygenation measured with near-infrared spectroscopy during normobaric and hyperbaric oxygen breathing in healthy subjects", European Journal of Applied Physiology, 2010, pp. 757-761, vol. 109, Springer.

Litscher et al., Transcranial Cerebral Oximetry in the Hyperbaric Environment, Department of Anesthesiology and Intensive Care Medicine, Biomed, Technik, 42 (1997) p. 38.

Litscher G., Schwarz G., Ratzenhofer-Komenda B., Kovacs H., Gabor S., Stolle-Jüttner F. M., "Transcranial Cerebral Oximetry in the Hyperbaric Environment", Biomedizinische Technik, 1997, pp. 38-41, vol. 42.

Masimo, Oxygen Reserve Index (ORi), Whitepaper, 2017.

McLeod et al., Measuring Cerebral Oxygenation During Normobaric Hyperoxia: A Comparison of Tissue Microprobes, Near-Infrared Spectroscopy, and Jugular Venous Oximetry in Head Injury, Departments of *Neuroanaesthesia and †Medical Physics & Bioengineering, The National Hospital for Neurology and Neurosurgery, University College London Hospitals & Centre for Anaesthesia, Anesth Analg 2003; 97:851-856).

Meter—Hyperbaric Oxygen in Resuscitation. Springer International Publishing AG 2017K.K. Jain, Textbook of Hyperbaric Medicine. 551-566.

Olafsdottir OB, Eliasdottir TS, Kristjansdottir JV, Hardarson SH, Stefansson E (2015) "Retinal Vessel Oxygen Saturation during 100% Oxygen Breathing in Healthy Individuals." PLoS ONE 10(6): e0128780. doi:10.1371/journal.pone.0128780.

Parnia. Cerebral oximetry—The holy grail of non-invasive cerebral perfusion monitoring in cardiac arrest or just a false dawn? Editorial / Resuscitation 83 (2012) 11-12. Oct. 27, 2011.

Patterson, et al., Time resolved reflectance and transmittance for the non-invasive measurement of tissue optical properties, Applied Optics, vol. 28, No. 12, Jun. 15, 1989 (p. 2331-2336).

(56)                 References Cited

OTHER PUBLICATIONS

Price et al. Response to Use of Cerebral Oximetry During Cardiac Arrest. Online Letters to the Editor. Mar. 2017, vol. 45, No. 3. e334-e335.

Putzer et al. Monitoring of brain oxygenation during hypothermic CPR—A prospective porcine study. Resuscitation 104 (2016) pp. 1-5.

Sanfilippoa et al. "Cerebral oximetry and return of spontaneous circulation after cardiac arrest: A systematic review and meta-analysis". Elsevier. Resuscitation 94 (2015) 67-72.

Suzuki, et al., A Tissue Oxygenation Monitor using NIR Spatially Resolved Spectroscopy, Proceedings of Optical Tomography and Spectroscopy of Tissue III, San Jose, California, SPIE vol. 2597, Jan. 1999.

Taccone. Cerebral oximetry during extracorporeal cardiopulmonary resuscitation. Critical Care 2013, 17:409 pp. 1-2.

Tajima et al. "Portable system for monitoring of regional cerebral oxygen saturation during prehospital cardiopulmonary resuscitation: a pilot study". Brief Communication. Acute Medicine & Surgery 2015; 2: 48-52.

Takegawa et al. Near-Infrared Spectroscopy Assessments of Regional CerebralOxygen Saturation for the Prediction of Clinical Outcomes in Patients WithCardiac Arrest: A Review of Clinical Impact, Evolution, and Future Directions. Frontiers in Medicine. Published: Oct. 29, 2020.

Parnia et al., "Cerebral Oximetry During Cardiac Arrest: A Multi-center Study of Neurological Outcomes and Survival" pp. 1-27.

China National Intellectual Property Administration: First Office Action issued for Application No. 202180087216.4, 28 pages, dated Dec. 3, 2025.

* cited by examiner

HHb Reduction During Normobaric Hyperoxia

FIGURE 4

START

Acquire full spectrum in 600 nm to 1000 nm range ⟋1302

Extract one or more chromophore concentration or change thereof ⟋1304

Derive absolute value of one or more physiological or health-related parameters (or change thereof) ⟋1306

SYSTEM AND METHOD FOR ADAPTIVE USER EXPERIENCE CYCLE PROFILING UNDER ANOMALOUS ENVIRONMENTAL RESPIRATORY CONDITIONS

FIELD OF THE DISCLOSURE

This application claims priority to U.S. Provisional Application No. 63/105,223 filed Oct. 24, 2020, and to U.S. Provisional Application No. 63/125,367 filed Dec. 14, 2020, the entire disclosure of each of which is incorporated herein by reference.

FIELD OF THE DISCLOSURE

The present disclosure relates to user safety equipment, and, in particular, to a system and method for adaptive user experience cycle profiling under anomalous environmental respiratory conditions, such as in hyperbaric or hypobaric environments.

BACKGROUND

The human body has largely evolved in ambient pressure of about 1 ATA (atmospheres absolute), and air oxygen concentration of about 21%. When the human body is exposed to an environment other than these normal conditions, referred to herein as anomalous respiratory conditions, the levels of inert and dissolved gases in the blood (as well as levels and types of hemoglobin) and, consequently, in the tissues, will be altered. This can lead to physiological impairments of different kinds.

Anomalous environmental respiratory conditions that can lead to altered physiology may include increased or decreased ambient atmospheric pressure. This can be a result of increased altitude, pressurization or depressurization in a hyperbaric chamber, or exposure to pressure at depths below seawater levels such as in mines or underwater.

Other conditions may also include, without limitation, a change in the gas breathed. This can result in any condition where a supplied air mix is delivered to a subject. This includes air mixes required for exposures for increased or decreased ambient pressures. Typically, an increased level of oxygen is deemed beneficial when ambient pressure is reduced. Likewise, an increased oxygen concentration is found beneficial for higher pressures to mitigate certain risk factors caused by other gases such as nitrogen for decompression sickness. At great pressures, levels of oxygen are often reduced to mitigate risks of oxygen toxicity. As well, increased levels of oxygen are often used for therapeutic purposes at either a normal ambient pressure of 1 ATA or at an increased pressure such as in hyperbaric treatment.

The above conditions may be relevant to many applications including: medical treatments, oxygen therapy, use of underwater breathing apparatus (open, closed, or semi-closed circuits), surface-supplied diving, aviation, space exploration, mining, activities at altitude, and/or any application involving an independent source or delivery of oxygen, etc.

Within the context of deep water diving, methods have been developed to design dive profiles (e.g. tables, models) that can outline safe diving practices applicable to most participants, or at least, serve to highlight potential risks and riskier diving practices.

Indeed, the physiological reaction to altered ambient conditions is a very complex dynamic that has yet to be fully understood. When prolonged exposure to high pressures was becoming feasible due to the availability of equipment and the need to do so, the need for a proper assessment of allowable exposure times to various conditions became quickly evident. This was a primary concern for prolonged exposure to underwater conditions, for example. Accordingly, military agencies around the world started testing the effects of various pressures and gas mixes for different times. As a result of these efforts, dive tables were created that cross-reference ambient pressure and oxygen concentration to safe exposure times for single and repeated dives. Repeated dives were affected by stored gases in the body. Initially, these tables were made assuming the diver was breathing air (21% O2). Over the decades since, more comprehensive tables have been developed that consider more exotic gas mixes that include, for example, helium. The underlying principle, however, for all these tables is to correlate three things: gas mix, depth, and exposure time.

There is an impact of the time taken to reach a certain depth on the exposure time allowable at that depth. Given the difficulty in taking this factor into account, tables typically assume the diver is exposed to the maximum depth for the entire time. This builds-in an inherent conservative factor. Corresponding dive profiles therefore follow a generally box-like profile as illustrated, for example, as profile 1702 of FIG. 17, effectively depicting a maximum total dive time for a given maximum planned dive depth.

Dive tables are still widely used, even outside the field of underwater diving. Hyperbaric medicine has established a set of "dive" profiles to be used for treatment in hyperbaric chambers. Indeed, hyperbaric medicine is still based on the use of "dive" tables, which will be referred to interchangeably herein as "hyperbaric cycle profiles".

This background information is provided to reveal information believed by the applicant to be of possible relevance. No admission is necessarily intended, nor should be construed, that any of the preceding information constitutes prior art or forms part of the general common knowledge in the relevant art.

SUMMARY

The following presents a simplified summary of the general inventive concept(s) described herein to provide a basic understanding of some aspects of the disclosure. This summary is not an extensive overview of the disclosure. It is not intended to restrict key or critical elements of embodiments of the disclosure or to delineate their scope beyond that which is explicitly or implicitly described by the following description and claims.

A need exists for a system and method for adaptive user experience cycle profiling under anomalous environmental respiratory conditions, such as in hyperbaric or hypobaric environments, that overcome some of the drawbacks of known technologies, or at least, provides a useful alternative thereto. Examples of such systems, devices and methods are disclosed herein, in accordance with difference embodiments.

In accordance with one aspect, there is provided a system for monitoring a user exposed to an anomalous environmental respiratory condition during an anomalous respiratory environment experience cycle having a maximum exposure risk defined therefor, the system comprising: an environmental sensor operable to monitor a respiratory environment parameter representative of the anomalous environmental respiratory condition that defines the experience cycle; a physiological sensor operable to concurrently monitor a physiological parameter representative of the user's cumulative physiological response to the anomalous environmental respiratory condition over time during the experience cycle; and a digital data processor operable to monitor said physiological parameter against a user-agnostic exposure risk profile designated to avoid exceeding the maximum exposure risk for a generic user exposed to the experience cycle, and identify therefrom an adapted user-specific exposure risk profile that deviates from said user-agnostic exposure risk profile to automatically output an adaptive exposure risk indicator in accordance with said adapted user-specific exposure risk profile that adaptively guides customization of the experience cycle while adhering to the maximum exposure risk.

In one embodiment, the digital data processor is operable to adaptively compute said user-agnostic exposure risk profile over time based on said respiratory environment parameter.

In one embodiment, the adaptive exposure restriction indicator comprises an adaptive maximum experience duration value.

In one embodiment, the adaptive maximum experience duration value is set for a given or a maximum depth.

In one embodiment, the experience comprises a hypobaric experience.

In one embodiment, the respiratory environment parameter comprises a current high altitude value and an exposure duration for said current high altitude.

In one embodiment, the experience comprises a hyperbaric experience.

In one embodiment, the respiratory environment parameter comprises a current depth and an exposure duration for said depth.

In one embodiment, the physiological parameter comprises at least one of a blood oxygen value or a tissue oxygen value.

In one embodiment, the physiological parameter comprises an absolute concentration of at least one of deoxyhemoglobin, oxyhemoglobin or dissolved oxygen.

In one embodiment, the physiological parameter comprises at least three of carbon monoxide, melanin, cytochrome oxidase, oxyhemoglobin, or deoxyhemoglobin.

In one embodiment, the physiological parameter comprises at least one of a blood inert gas value or a tissue inert gas value.

In one embodiment, the digital data processor automatically evaluates a user's current condition based on said physiological parameter and, upon said current condition being automatically evaluated as substantially worse than an anticipated condition for a current cumulative exposure, automatically adapts said user-specific exposure risk profile to reflect an increased user-specific cumulative exposure risk for the user and thereby reduce an overall acceptable cumulative exposure setting associated with the experience cycle.

In one embodiment, the digital data processor automatically evaluates a user's current condition based on said physiological parameter and, upon said current condition being automatically evaluated as substantially better than an anticipated condition for a current cumulative exposure, automatically adapts said user-specific exposure risk profile to reflect a reduced user-specific cumulative exposure risk for the user and thereby increase an overall acceptable cumulative exposure setting associated with the experience cycle.

In one embodiment, the digital data processor is further operable to automatically evaluate said adapted user-specific exposure risk profile over multiple exposure cycles to predictively output subsequent adapted user-specific exposure risk profiles.

In one embodiment, each said adapted user-specific exposure risk profile is digitally evaluated to update a user-specific physiological response model representative of the user's anticipated response to said multiple exposure cycles, and wherein said user-agnostic exposure risk profile is automatically adapted for a subsequent exposure cycle as a function of said user-specific physiological response model.

In one embodiment, the physiological sensor comprise an infrared or near-infrared probe.

In one embodiment, the physiological sensor comprises a broad spectrum oximeter.

In accordance with another aspect, there is provided a computer-implemented method, implemented by one or more digital processors, for monitoring a user exposed to an anomalous environmental respiratory condition during an anomalous respiratory environment experience cycle having a maximum exposure risk defined therefor, the method comprising: receiving as input, via an environmental sensor, a respiratory environment parameter representative of the anomalous environmental respiratory condition that defines the experience cycle; concurrently receiving as input, via a physiological sensor, a physiological parameter representative of the user's cumulative physiological response to the anomalous environmental respiratory condition over time during the experience cycle; and digitally monitoring said physiological parameter against a stored user-agnostic exposure risk profile designated to avoid exceeding the maximum exposure risk for a generic user exposed to the experience cycle, and identifying therefrom an adapted user-specific exposure risk profile that deviates from said user-agnostic exposure risk profile; and automatically outputting an adaptive exposure risk indicator in accordance with said adapted user-specific exposure risk profile that adaptively guides customization of the experience cycle while adhering to the maximum exposure risk.

In accordance with another aspect, there is provided a non-transitory computer-readable medium comprising digital instructions for implementation by one or more digital processors for monitoring a user exposed to an anomalous environmental respiratory condition during an anomalous respiratory environment experience cycle having a maximum exposure risk defined therefor, by: accessing a respiratory environment parameter representative of the anomalous environmental respiratory condition that defines the experience cycle; concurrently accessing a physiological parameter representative of the user's cumulative physiological response to the anomalous environmental respiratory condition over time during the experience cycle; and digitally monitoring said physiological parameter against a stored user-agnostic exposure risk profile designated to avoid exceeding the maximum exposure risk for a generic user exposed to the experience cycle, and identifying therefrom an adapted user-specific exposure risk profile that deviates from said user-agnostic exposure risk profile; and automatically outputting an adaptive exposure risk indicator in accordance with said adapted user-specific exposure risk profile that adaptively guides customization of the experience cycle while adhering to the maximum exposure risk.

Other aspects, features and/or advantages will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein:

FIG. 4 is an exemplary plot of the change in time of the relative absorbance of deoxyhemoglobin as measured by NIRS of an individual breathing a series of different gas mixtures containing higher than normal concentrations of oxygen (hyperoxic mix), in accordance with one embodiment;

Figure 1:
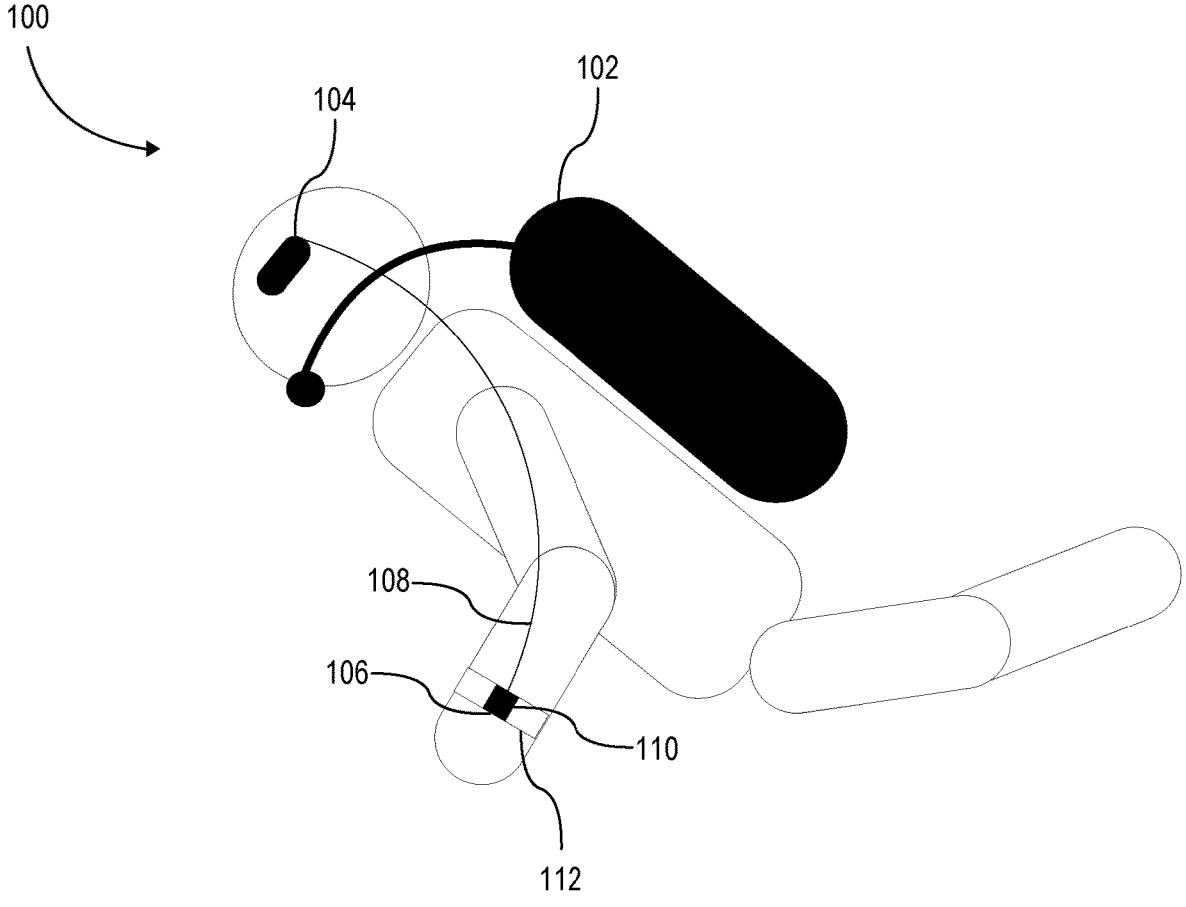
FIG. 1 is a schematic diagram of a cerebral blood oxygenation monitoring system used by a scuba diver, in accordance with one embodiment.

Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood elements that are useful or necessary in commercially feasible embodiments are often not depicted in order to facilitate a less obstructed view of these various embodiments of the present disclosure.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

Various apparatus and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

Unless defined otherwise, all technical and scientific terms used herein have the same meaning as commonly understood by one of ordinary skill in the art to which this invention belongs.

Throughout the specification and claims, the following terms take the meanings explicitly associated herein, unless the context clearly dictates otherwise. The phrase "in one of the embodiments" or "in at least one of the various embodiments" as used herein does not necessarily refer to the same embodiment, though it may. Furthermore, the phrase "in another embodiment" or "in some embodiments" as used herein does not necessarily refer to a different embodiment, although it may. Thus, as described below, various embodiments may be readily combined, without departing from the scope or spirit of the innovations disclosed herein.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references unless the context clearly dictates otherwise. The meaning of "in" includes "in" and "on."

The term "comprising" as used herein will be understood to mean that the list following is non-exhaustive and may or may not include any other additional suitable items, for example one or more further feature(s), component(s) and/or element(s) as appropriate.

The systems and methods described herein provide, in accordance with different embodiments, different examples of systems and methods for adaptive user experience cycle profiling under anomalous environmental respiratory conditions, such as in hyperbaric or hypobaric environments. Namely, some embodiments provide examples of an adaptive hyperbaric or hypobaric cycle profile management system and method, in which physiological data can be acquired during a particular cycle to dynamically adjust a designated, prescribed, preset or anticipate cycle profile to address a particular user's physiology while exposed to such anomalous respiratory environments. For example, a hyperbaric or hypobaric experience, and a user's corresponding respiratory physiology, may vary from user to user based on experience, health and/or fitness, or again for a given user between cycles depending a number of conditions, which may include, but are not limited to, physiological, health, experiential, environmental and/or other such conditions as may apply and/or vary from one cycle or session to the next.

As will be described in greater detail below, while focus will be made on hyperbaric cycles experienced during underwater diving, applicability of the herein-described solutions are not limited as such. For instance, hyperbaric cycles may be experienced in different environments, as well as simulated in different medical or treatment centers. Likewise, the herein-described embodiments may also be applied to hypobaric experiences, or again for users exposed to other such or similar anomalous respiratory conditions. Accordingly, while examples are illustrated herein within the context of a diving experience, whereby a diver can be subject to varying external pressures as they dive to and from different depths for different time durations, the herein-described solutions may equally be applied to hyperbaric treatment chambers or the like in which varying external pressurizations may be applied according to prescribed treatment protocols, for example, or again to different hypobaric experiences such as to simulate or experience high altitude conditions. Accordingly, the term "anomalous environmental respiratory conditions" and "user experience cycles" related thereto, will be used herein to describe a particular anomalous pressurization and/or oxygenation profile over time defined by a series of pressurizations and/or oxygenations, and corresponding exposure times planned or logged at or for each such anomalous environmental respiratory conditions.

In some embodiments, it will be appreciated that different pressurization periods may be defined by particular external pressurization ranges or values, as can such periods be defined by gradual variations therein, for example, to reflect a progressive pressurization or depressurization (e.g. descent and ascent in a diving environment, unpressurized travel at high altitude, etc.). Furthermore, a pressurization cycle may be defined by a number of discrete or continuous environmental measurements/values over time (depth/pressure, ambient temperature, etc.), to be processed in concert with corresponding physiological measurements (e.g. arterial and/or venal oximetry, heart rate, pulse, body temperature, respiration rate, etc.).

In one particular embodiment, a computational system and method are provided for the provision of real-time physiological monitoring for the purposes of updating or otherwise modifying a standard, planned or prescribed dive profile to enhance a diver experience and/or safety by accounting for real-time physiological indicators as to the user's actual physiological experience during a particular hyperbaric cycle, thus providing a significant improvement in dive profiling.

For instance, in some embodiments, a dive computer can allow for the use of physiological models, and real-time recalculation and profiling based on continuous measurement of depth and exposure time. Indeed, dive algorithms can be designed based on models of how changing depth will affect allowed exposure times. That is, it allows for a better resolution of the profile calculation based on depth and time for a specific gas mix, and thus provides for a significant improvement over the max-depth profile illustrated as profile 1702 of FIG. 17. Indeed, a dive computer carried by a diver can allow for calculations to be made as to the actual time spent at each depth and allow for a more optimal calculation of exposure times without compromising safety. One such exemplary profile for a complex dive is illustrated as profile 1704 of FIG. 17, which more specifically reflects distinct descent and ascent speeds, as well as time spend at various depths up and down during the entire dive.

These calculations, however, are again based exclusively on environmental variables such as gas mix, depth, and time. Indeed, these calculations are done the same way for all divers regardless of their physiology. The models are based on average responses such as those built-in to set dive tables. Safety buffers are added for a conservative approach if desired. It has however been demonstrated scientifically that different divers will react differently to the same environmental conditions. Also, the same diver will not react the same way to the same environmental conditions from one dive to the next. The reasons for this are not well understood.

To mitigate risks while enhancing or optimizing dive profiles, some of the herein-described embodiments further allow for the continuous (or semi-continuous) measurement of physiological parameters indicative of the physiological state of the diver. These parameters include but are not limited to: oxygenation levels indicative of both hypoxic and hyperoxic states (e.g. as described in further detail below to provide detailed information on consumed and dissolved blood oxygen levels indicative of actual oxygen toxicity risks), heart rate, breathing rate, and body temperature.

In some embodiments, these measurements are synchronous to allow enhanced correlation between them and the physiological state of the diver.

In some embodiments, other variables can also be derived and used in the assessment, such as heart rate variability, VO2 max, etc. For example, the VO2 max is based on the Fick equation when maximal exertion is reached as defined by the following equation:

$$VO_2 = Q \cdot (C_aO_2 - C_vO_2)$$

where Q is the cardiac output, $C_aO_2$ is the arterial oxygen content, and $C_vO_2$ is the venous oxygen content.

In real-time, it may be difficult to directly measure $(C_aO_2 - C_vO_2)$ as it requires measurement in the arterial and venous blood. Tests such as the heart rate ratio method, Cooper Test, etc., have been devised to approximate this value.

However, utilizing a spectroximetry probe, as further described below, a more direct measure of this value can be achieved continuously and in real-time.

Accordingly, by actively taking these physiological parameters into account during a particular hyperbaric cycle, the hyperbaric cycle profile monitoring system as described herein can actively compensate for the variability of the diver's reaction to the same conditions and base actionable decisions more tailored to the individual's real condition at the time. Actionable decisions can include, but are not limited to, indicators encouraging the diver:

to surface or reduce depth, or allow increased depth
to prolong or reduce exposure time
to alter gas mix
to reduce physical activity
etc.

Accordingly, while prior efforts to improve dive cycle profile resolution relied exclusively on environmental conditions (pressure, running time, etc.), the systems and methods as described herein add an additional physiological layer to profiling that can adjust the current models in real-time and as a function of a current user experience and physiology.

The approach of Physiologically Adaptive Dive Profiling (PADP) allows the generation of new processes that account for the actual physiological parameter being measured in real-time under the environmental stresses the subject is subject to, whereas previous models account only for current depth and time and make assumptions based on theoretical models of the physiological reactions to these environmental conditions.

Figure 17:
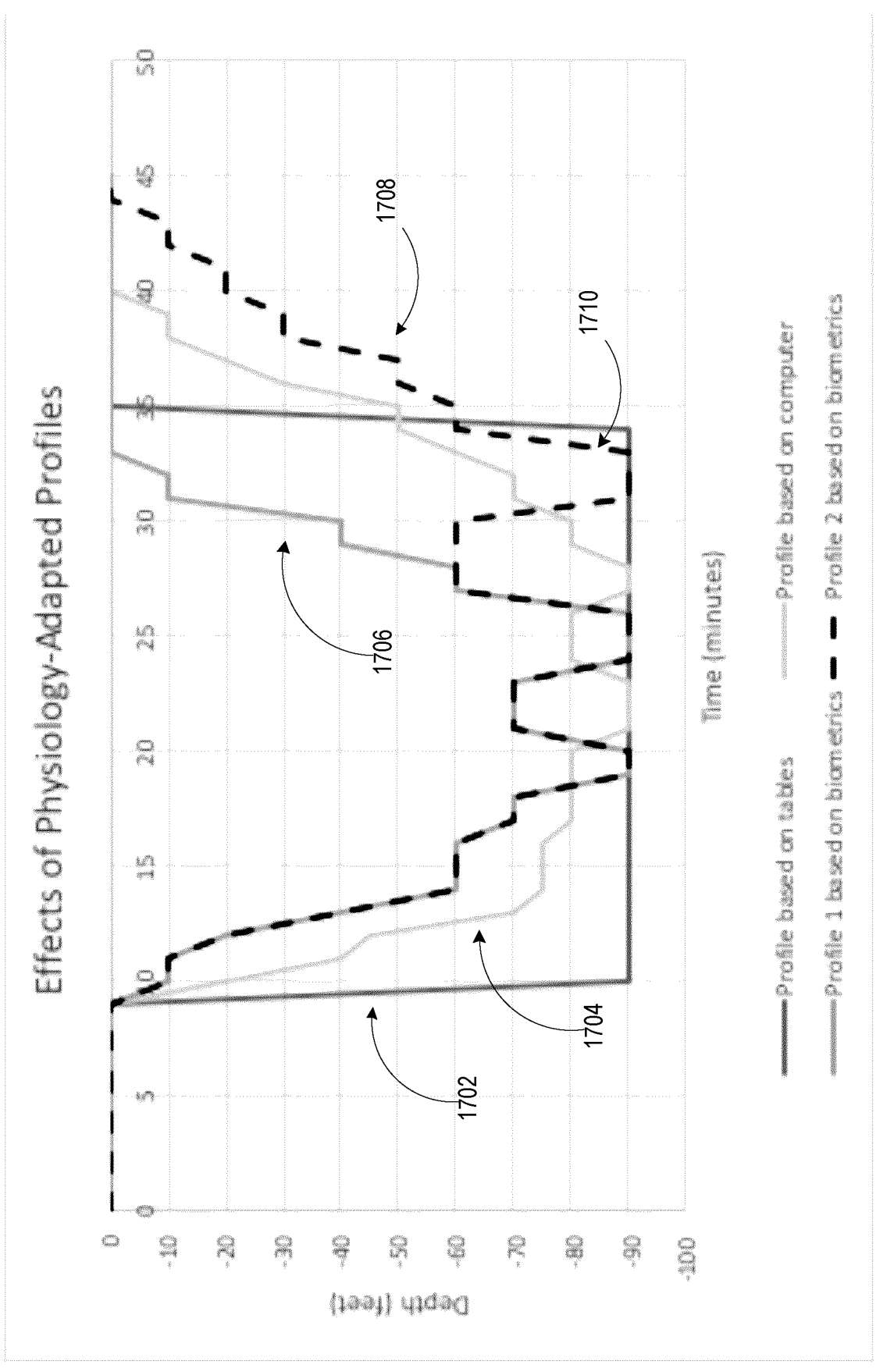
FIG. 17 is a combined plot showing an exemplary plot of a traditional dive profile based on a designated dive table, an enhanced dive profile based on computationally enhanced depth and exposure data for a particular dive plan, and comparative user-specific dive profiles based on real-time physiological data for distinct dives.

Accordingly, PADP results may include, but are not limited to:

enhanced prediction of hazardous health states
more optimal physical performance
allow the ability to train Machine-Learning algorithms (Artificial Intelligence) to generate a model tailored to individual divers unique customized adapted profile based on current conditions
tracking of performance enhancement over time
detection of anomalies based on history of physiological response
objective comparison between diver performances FIG. 17 provides an exemplary plot of an enhanced hyperbaric (dive) cycle profiles based on physiological profiling, in accordance with one embodiment. For example, profiles 1706 and 1708 (dashed) illustrate comparable adaptive dive profiles in which respective divers (or a same diver on separate occasions) initially execute a same dive plan, but with the latter (1708) being permitted to execute an additional descent 1710 to extend their dive time given favourable physiological readings (or alternatively, the former (1706) is instructed or encouraged to cut a planned dive short given unfavourable physiological readings).

Indeed, as noted above, stresses on a user's physiology during a hyperbaric cycle are highly dependent on environmental conditions as well as other less understood factors. For example, a subject experiencing unexpected events can experience stress that will greatly alter the body's reaction relative to how it would have experienced the same environment without the stress-causing event. The physiological response can then significantly alter the body's tolerance levels before hazardous health conditions are reached.

This is true for diving as well as other applications in which an individual experiences abnormal, extreme, or harsh environmental conditions. Examples of these environmental conditions include, but are not limited to, increased or decreased partial pressures of specific gases such as nitrogen and oxygen, or high or low atmospheric pressures, to name a few. Such conditions can be found underwater, at altitude, in aviation, firefighting, mining, etc.

Again, for the sake of illustration, focus is made herein to underwater diving, which provides a good example of a situation in which significant changes in environmental factors generally lead to corresponding physiological changes.

To illustrate the benefits of the proposed profiling methodology, the plots at FIG. 17 show a series of exemplary dive profiles based on the use of traditional dive tables (1702), dive computers (1704), and the proposed physiology-adapted profiling method described herein (1706 and 1708).

The following further illustrates the advantages of the PADP approach for a diver who initially plans to dive to a maximum depth of 90 feet. A standard profile (1702) is illustrated in which an allowed dive time is determined using traditional dive tables. In this case, the maximum depth is assumed for the entire dive time when planning according to these tables. The dive plan cannot be changed during the dive since no measurements are taken of what the diver is actually doing. The plan must be followed and is based on the conservative assumption that the diver will be at the maximum depth for the duration of the dive. The assumed gas residuals in the body are derived from this assumption as well regardless, for example, of the level of exertion during the dive and the body temperature of the diver which are known to affect these residuals.

In a first improved profile (1704), a more realistic dive profile down to 90 feet is illustrated. As shown, the diver does not remain at 90 feet for the duration of the bottom time but has two periods when that maximum depth is reached. The average depth is therefore less than the assumed depth using traditional tables. In this case, a dive computer can track the diver's depth and time and derive a more accurate estimation of their effects on the body based on this higher level of resolution of depth/time measurements. This methodology however basically works in the same way as the dive table in that it is based principally on the depth and time. The finer tracking of depth and time can however benefit the diver as it can either extend the allowable dive time or result in the accurate assessment of less impact on the body compared to the conservative dive table approach. The effects on the body are however assumed to be the same for all individuals wearing the dive computer and using the same algorithm with the same settings.

In comparison, the proposed physiology-adapted profiling allows the creation of new approaches that can take into account the physiological effects that vary from one diver to another when performing identical profiles. It has also been shown that the same diver can react differently when performing the same level of exertion under the same conditions from one instance to the next. These physiological effects can include level of absorption of inert gas, sensitivity to narcosis, onset of decompression sickness, sensitivity to O2 toxicity, etc. Physiological effects immediately affect the diver's allowable depth and time. As such, in the illustrated physiology-adapted profile 1706, the diver can be found to be reacting adversely to their exposure after their second excursion to 90 feet. In this case, the physiology-adapted dive computer issues an indication to the diver to surface before a hazardous health condition is reached. This hazardous state would not have been predictable using the dive tables or a conventional dive computer. Meanwhile, in the comparable physiology-adapted profile 1708, another diver (or the same diver on a different identical dive) does not exhibit the same adverse physiological indications and can thus be permitted to complete a third excursion to 90 feet even though the initial profile is identical to the otherwise time-restricted profile 1706. The resulting dive can even safely be extended beyond the time limits that would otherwise have been set based on dive tables or environment-tracking dive computers (1702, 1704).

Accordingly, embodiments as described herein may be configured to measure variables that include both physiological and environmental indicators. The environmental indicators (or measurables) generally consist of all parameters of interest that are not specific to the subject diver, such as depth, time at each depth, gas mix used for breathing, ambient temperature, etc. Meanwhile, physiological factors or indicators may include, but are not limited to:

O2 uptake (for example by observation of O2 levels in the arterial and venous blood);

Tracked hyperoxic levels over time (i.e. tracked oversupply of O2 in the blood in the form of dissolved O2 and oxyhemoglobin, which serves to track stored levels);

O2 arterial saturation which is indicative of hypoxic levels (i.e. drop in arterial oxyhemoglobin);

Breathing rate (which is indicative of gas volume in lungs, O2 replenishing, level of exertion, and reaction of the body to health state, etc.);

Pulse rate (which is indicative of the level of blood volume that tissue is exposed to, level of exertion, and reaction of the body to health state, etc.);

Core body temperature (which affects the level of gas absorption and metabolism, etc.);

Body orientation in 3D space (head up, head down, upright, supine, etc.);

Etc.

Correlations between the physiological indicators and the experienced environmental factors in which they are acquired (depth, time, etc.) are indicative of the diver's state of health that can vary from one dive to the next depending on many factors. For example, the psychological state of the diver (stress for example) can affect the level of breathing, heart rate, and tendency of gas absorption. This in turn can increase the supply and storage of O2 thereby applying higher than usual (for the diver in question) gas tension on critical tissue (central nervous system for example). This higher state of risk can be detected via the combination of environmental and physiological indicators. These would be completely overlooked by plans based on dive tables or dive computer that rely solely on diver-agnostic (i.e. environmental) measurables. Conversely, in the herein-described embodiments, the particular instance of abnormal physiological indicators (as they correlate to the environment) can be measured in real-time and allow the adaptation of the dive profile to compensate. The pattern of physiology vs. environment over time for an individual diver can be recorded and used for comparative purposes (for example to evaluate evolution in performance or instance of abnormal state).

In some embodiments, comparisons can be done based on historical physiological variations that have been acquired for that individual diver. For example, a Machine-Learned algorithm can be tailored for the individual diver in order to assess and predict a physiological state based on a pre-programmed or planned dive that was intended to be completed. The algorithm can then warn the diver that given the current state, future instances in the planned dive profile will require alteration and advise on what the alterations will be. Recommendations for immediate changes can also be derived and communicated to the diver in order to avoid those future hazardous states.

Conversely, the herein-described methodology can be used to detect a higher than usual (for the specific diver) performance. This can be a result of an optimal psychological state of mind during the dive, or recent physical training for example. In this case, the diver's physiological response to environmental factors will be reflected in, for example, reduced heart rate, reduced and deeper breathing patterns, lower O2 uptake, etc. This will affect absorbed and stored gas molecules and reduced partial pressures in tissue. As a result, the adaptive model can safely advise the diver that normal dive limits can be extended and by how much (in terms of depth and time for example). Alternatively, the algorithm can indicate a lower level of residuals after the dive should the diver choose not to alter the pre-planned dive and thereby benefit from these reduced residuals on the subsequent dive.

The methodology is further particularly well suited, in some embodiments, to recognize when the diver is in physical distress, such as when experiencing convulsions due to O2 toxicity. In this case, the device can engage an alarm to fellow divers or to support staff at the surface through means of telecommunicated alarms, or optical warning signals.

As detailed above, diver-agnostic dive profiling methods rely on measuring a series of stand-alone parameters, whereby thresholds can be set for one or a set of these parameters and set equal for all divers or subset of divers (i.e. male, female, weight, height, etc.). While some diver-agnostic dive profiling computers also acquire basic physiology data (e.g. heart rate, breathing rate, saturation, etc.), the applied dive profiling methodologies remain diver-agnostic in that they nonetheless exclusively rely on averages for a large number of divers to set each dive profile irrespective of current, real-time diver-specific physiological conditions.

In comparison, the herein-proposed Physiology-Adapted Dive Profiling methodology relies on observable patterns of changes between measurable physiological indicators and environmental factors. In other words, changes in physiology measurables as a function of measured changes in environment can yield greater insight as to the diver's physiological experience that go beyond stand-alone indicators on environment or physiology. Indeed, the dynamics between physiology and environment as the user's experience evolves across multiple environment conditions can reveal a more accurate risk assessment and thus permit for adaptive profiles in real-time.

In general, while the pattern of how the physiology indicators react to a changing environment will be similar amongst individuals (due to similar overall physiology), these can also demonstrate unique features that can act as "fingerprint" patterns for individual divers. This can thus allow for the personalization of the dive model and enable predictive capabilities of future physiological states, including predictions of hazardous conditions before they occur, at an individual level as compared to standard averages derived from a large number of divers.

Figure 18:
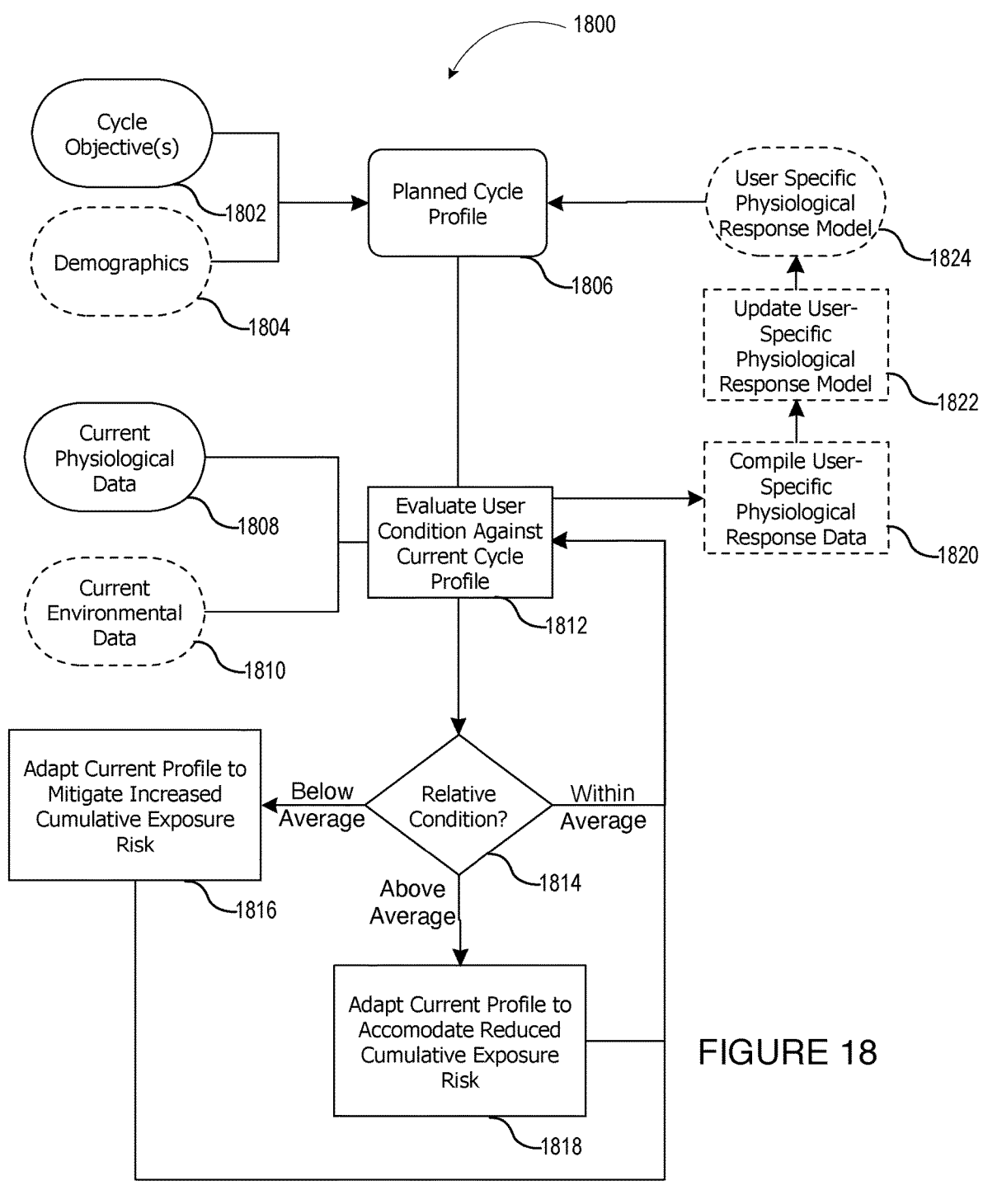
FIG. 18 is a schematic diagram of an adaptive anomalous respiratory environment cycle profiling process, in accordance with one embodiment.

With reference now to FIG. 18, and in accordance with one embodiment, an illustrative implementation of a device or system as described herein, will now be described. In this automated or semi-automated process, referenced using the numeral 1800, a user experience to be held under an anomalous respiratory conditions, for instance, within the context of an experience cycle (e.g. hyperbaric cycle, hypobaric cycle, etc.) 1802 is defined via one or more objectives. For example, a hyperbaric cycle may be defined by an objective dive cycle at a particular maximum depth. Other attributes such as user demographics (age, sex, fitness level, etc.) 1804 may also optionally be taken into account in defining a planned cycle profile 1806. Again within the example of a dive profile, this may be represented by a maximum total dive time for the objective maximum dive depth. Naturally, other parameters may also be considered, such as for example, the type/content of gas being supplied during the cycle, relative temperatures, number or parameters associated with recently completed cycles, etc.

Once the planned cycle is initiated (e.g. dive commences), a cycle monitoring device may be configured to regularly evaluate a condition of the user at 1812 based on input physiological data (e.g. blood/tissue oxygenation data such as monitored via acquisition of deoxyhemoglobin concentration variations, derived dissolved oxygen concentrations, tissue oxygenation values; blood/tissue inert gas content data; etc.) 1808 and optionally current environmental data 1810. For example, again within the context of a dive profile, a convention dive profile management device may regularly recalculate a dive profile based on actual time spent at each depth during a descent and/or while lingering at any particular depth. This recalculation may result in an increase or decrease of the total dive time, for example, depending on a descent speed or actual time-depth profile associated with the ongoing cycle. This can thus result in a more precise safe-diving profile as illustrated as profile 1704 of FIG. 17. In this particular example, however, optionally irrespective of such environmental calculations, a user's current physiological condition (e.g. blood or tissue oxygenation rating/index, relative or cumulative decrease in deoxyhemoglobin concentrations, etc.) may be monitored and evaluated. For example, the device at 1814 may evaluate whether the user's current condition, given cumulative exposure to the anomalous respiratory conditions to date during the planned or current dive profile, is relatively consistent with an expected (e.g. average or range) condition for this current profile, in which case the current cycle profile is maintained and re-evaluated periodically at 1812, is relatively below anticipated conditions at 1816 in which case the current cycle profile is automatically adapted to mitigate increased cumulative exposure risks, or is relatively above anticipated conditions at 1818, in which case the current cycle profile is automatically adapted to accommodate reduced cumulative exposure risks (e.g. allocate greater exposure time thresholds). In each case, the evaluation cycle at 1812 may be periodically implemented as a function of updated physiological and/or environmental parameters. Different techniques may be employed to compute such comparative analyses, such as comparing current values or indexes with established threshold, ranges or trends, or again comparing physiological signal signatures, variances or markers with corresponding established standard signatures, variances or markers.

In one exemplary embodiment, the system/device may be further operable to track and account for historical user data either in real-time, or from cycle to cycle. For example, again within the context of the illustrative embodiment of FIG. 18, evaluation of the user's condition against a current profile and/or current or accumulated environment data, may be compiled in a user-specific physiological response repository 1820. This response data can then be used to update a user-specific physiological response model 1824 at 1822, which can be used to populate or guide planning or implementation of future cycle profiles 1806. Naturally, while user-specific data may be used to update a user-specific model, such data may also be used in combination with other user data to improve and expand global or demographically-defined cycle profiles, parameters, thresholds and limitations, for example.

As introduced above, in order to provide enhanced physiological tracking, for example, in preventing or reducing the risk of oxygen toxicity by dynamically adjusting a preset or intended dive profile, physiological data may be acquired using one or more physiological sensors. In one particular embodiment, an oximetry sensor is used to gather real time blood oxygenation data in evaluating the user's consumption and response to delivered oxygen under pressure.

For example, pulse oximetry is often used in health-related systems to monitor blood oxygenation. This typically works by emitting NIR light into tissues, measuring the corresponding transmitted or reflected light at two distinct wavelengths, and deriving from changes in absorbance a corresponding change in oxyhemoglobin, for instance, in the form of an estimate from relative variations, calibration or via index-tables.

In general, conventional oximetry relies on measurement ratios for 2 blood-oxygen-related absorption wavelengths (oxyhemoglobin and deoxyhemoglobin) to produce useable, but at times limited results. Indeed, absorption ratios lose specificity in observing actual or absolute blood oxygen concentrations and neglect the finer detail otherwise available using techniques as described herein, in accordance with some embodiments, that probe and analyze greater portions of the blood or probe tissue's absorption spectrum. Moreover, since it relies on indices that are derived principally as ratios and are relative to baseline measurements, conventional oximetry also requires calibration (or the use of look-up tables) to associate a measured index with a saturation level, further restricting use and applicability. Furthermore, conventional pulse oximeters often do not provide reliable readings when saturation is low, and require that a pulse or heart beat be continuously and accurately detectable. While spatially-resolved spectrometry can provide further information as it invokes a spatial investigation, it remains constrained to the analysis of relative spatially-resolved concentration ratios, and thus remains unable to extract absolute total concentrations.

Accordingly, in some embodiments, improved oximetry techniques are employed, such as that described in Applicant's co-pending U.S. application Ser. No. 17/046,704, the entire contents of which are hereby incorporated herein by reference, that can more readily extract useful blood oxygenation details otherwise unavailable using standard pulse oximetry. For example, measuring and monitoring variations in an absorption or transmission spectrum related to deoxyhemoglobin and/or hemoglobin over time may lead to an accurate measure of deoxyhemoglobin and/or hemoglobin concentrations (as opposed to mere relative saturation measurements) that can be used to accurately characterize oxygen consumption, transport and dissolution in the blood and thus provide a clear indicator as to potential risks of oxygen toxicity, for example, such as manifested by hyperoxia, for example. Indeed, available pulse oximetry solutions are generally unconcerned with, and thus generally fail to provide useful indicators as to risks of hyperoxia given their general application in conventional (standard pressure) medical practices. However, within the context of a diver or patient experiencing a hyperbaric environment, the risks associated with hyperoxia become far more relevant. Accordingly, in accordance with some embodiments, an optical probe as described in Applicant's co-pending application can be used to monitor variations in direct or derived deoxyhemoglobin and/or oxyhemoglobin concentrations, dissolved oxygen concentrations, and related measurements, to assess and issue an alert or indicator related to a current or forecasted risk of blood oxygen toxicity, namely of hyperoxia.

For completeness, in some embodiments, the systems and methods described herein can provide, in accordance with different embodiments, means for monitoring for abnormal blood oxygenation levels of a user, for example partaking in an activity while exposed to partial oxygen pressures deviating from the normal value of 0.21 at 1 ATA. Namely, the methods and systems, according to different embodiments, may be used to monitor blood oxygen content (bounded to hemoglobin and/or dissolved in the blood or tissues) and assess accordingly a health-related risk of hyperoxia and/or hypoxia; or optionally derive therefrom assessment of the user's cognitive level. As a result of this assessment, as introduced above, a dive profile may be actively altered in real-time so to account for variability between users and/or between cycles for a same user. Namely, by actively monitoring blood oxygenation parameters and profiles as described below, and comparing such parameters and/or profiles against standard, expected or planned profiles for a given or calculated hyperbaric cycle (e.g. dive plan), the system may automatically detect or identify a physiological response variance that can be used to alert, prescribe or suggest that the ongoing hyperbaric cycle plan be altered. As noted above, such alterations may include a recommendation that a diver ascend sooner than originally anticipated, spend less time at a particular depth, adjust a breathing gas mix, reduce their level of exertion, or the like, or again, allow for such parameters or conditions to be increased (greater depth, time, exertion, etc.) given a particular user's above-average experience, constitution or physiological affinity for hyperbaric activities or treatments.

In the following examples, according to some embodiments, the user is constrained either to wear a breathing mask/apparatus or is located in a sealed and pressurized environment. This includes the user breathing gas that is either a hyperoxic or hypoxic mix (at any pressure) or normal air (e.g. 21% $O_2$) at a higher or lower pressure than atmospheric pressure. Examples of applications include, without limitation, underwater or deep diving, any activity in a hyperbaric chamber or deep-water bell or habitats (including hyperbaric medicine), any activity in a pressurized cockpit (e.g. piloting aircrafts, spacecrafts) and EVA suits or similar. Other users may include monitoring oxygenation during first-aid (including using defibrillators), for firefighters, soldiers, etc.

In some embodiments, the systems and methods described below rely on various oximetry techniques (e.g. pulse or cerebral oximetry, etc.) to identify and quantify the presence of one or more chromophores' molecules in the user's blood. The measured attenuation (or optical density) measured from one or more oximetry probes may be used to derive a corresponding oxygen partial pressure and/or relative oxygen concentration in said blood. This includes, in some embodiments, quantifying the concentration of dissolved $O2$ (dO2) by monitoring the oxygen input, levels of mixed blood saturation, combined with a physiological model of oxygen transport in the body. Thus, the systems and methods described herein, in accordance with some embodiments, may be used to monitor in real-time a user's health risk of hyperoxia and/or hypoxia in such operating environments.

In some embodiments, the oximetry technique used is based on near-infrared spectroscopy (NIRS). These are based on the fact that distinct biological molecules change their optical properties when binding to oxygen. This phenomenon is caused by the fact that chromophores such as oxygenated hemoglobin (oxyhemoglobin or O2Hb) differs in parts of its absorption pattern from de-oxygenated hemoglobin (deoxyhemoglobin or HHb), and thus in their apparent optical spectrum. These optical differences have been exploited and are now clinical standard application in pulse oximetry, where usually two or three distinct wavelengths are used in combination with pulse plethysmography to measure the arterial hemoglobin oxygen saturation. Visible light penetrates tissue only short distances, since it is markedly attenuated by several tissue components, which absorb or scatter visible light. However, in the near-infrared (NIR) spectrum (ranging from 700 to 1100 nm) photons are capable of deeper penetration of several centimeters or more. Moreover, NIR beams may also penetrate bones, which is prerequisite for trans-cranial cerebral oximetry for example, although generally speaking other probe locations may be used. Aside from the advantage of relatively deep penetration of several centimeters, the NIR spectral region is also characterized by typical differences in the spectrum of oxygenated and deoxygenated hemoglobin, for example. As mentioned above, other chromophores present in the blood that may be monitored using these techniques usually comprise O2Hb and HHb, but other molecules may be monitored as well, for example (and without limitation) cytochrome c oxidase, carbon monoxide (CO), methemoglobin, etc.

In some embodiments, it may also be that one or more chromophores being monitored have more complex absorption spectra, such as a broader spectrum and/or comprising of two or more peaks. Generally speaking, the herein described embodiments are not limited to using one to three wavelengths, but may use as many wavelengths as needed to properly characterize the presence of one or more chromophore molecules present in the user's blood. To achieve this, any number of additional wavelengths may be used (e.g. any wavelength ranging from 600 to 1100 nm). Furthermore, measuring such components may result in overlapping spectra features for two or more components. In this case, multivariate statistical analysis methods may be applied to extract a singular signature for each overlapping component. For example, these may include, without limitation: linear (or non-linear) multivariate regression (MVR), principal component analysis (PCA), principal component regression (PCR), discriminant analysis (DA), hierarchical cluster analysis (HCA), soft independent modeling of class analogy (SIMCA), or similar.

Exploiting these natural characteristics for regional oximetry such as cerebral oximetry (or other), a prototypical NIRS probe functions as follows: A light source (e.g., one or more LEDs of different wavelengths) generates NIR light, concerning the spectrum centered around characteristic wavelengths. The emitted beam is directed into the tissue of interest via a (usually cutaneous attached) probe. The probe is usually attached to the skin above the tissue of interest. Respective stickers of the probes serve to stabilize the probe's position over longer periods, but also restrict entrance of ambient light into the measurement photon pathway. Transcutaneous NIRS is noninvasive and the applied light intensities are not harmful to the tissue, not causing skin burns even if applied for a longer period.

Generally, the change in molar concentration of the monitored chromophore (for example O2Hb or HHb) may be calculated from the measured change absorbance/attenuation of the NIRS signal by using a physical model of light diffusion and attenuation in organic tissues derived from radiative transfer theory (e.g. using a modified Beers-Lambert law or similar; for example see: Susumu Suzuki, Sumio Takasaki, Takeo Ozaki, and Yukio Kobayashi "Tissue oxygenation monitor using NIR spatially resolved spectroscopy", Proc. SPIE 3597, Optical Tomography and Spectroscopy of Tissue III, (15 Jul. 1999); doi: 10.1117/12.356862 and Michael S. Patterson, B. Chance, and B. C. Wilson, "Time resolved reflectance and transmittance for the non-invasive measurement of tissue optical properties," Appl. Opt. 28, 2331-2336 (1989), the entire contents of each of which are hereby incorporated herein by reference).

Furthermore, in some embodiments, the molar concentration may then be used to assess, for example, the dissolved oxygen content in the user's blood (dO2). Indeed, oxygen is found in two forms in the blood: in solution (or dissolved) and bound to hemoglobin. Since dissolved oxygen may accumulate in the blood and be discharged at a later time when partial oxygen pressures are lowered, such an assessment may be important for assessing a user's risk level. In some embodiments, a physiological model may be used to calculate the concentration of dO2 (or change thereof). For example, such a model may determine, in some embodiments, the component or fraction of the inhaled oxygen that is absorbed into the blood stream from measurement of the partial pressure of the inhaled gas mix since the inhaled and absorbed gases will reach equilibrium across the alveolar-blood interface. Current knowledge of physiological processes (such as Fick's diffusion law, O2 solubility, etc.) allows for this evaluation. For example, assuming that the oxygen that enters the blood stream is either bounded to hemoglobin or remains in a dissolved state, changes in the oxy and deoxyhemoglobin concentrations in the target mixed blood volume can be evaluated. This in turn allows a determination of the component that remains in the dissolved state under the assumption that other physiological parameters such as total hemoglobin number, blood volume, etc., remains nominal and constant. In some embodiments, such a model may use additional parameters such as the oxygen intake (e.g. quantity of oxygen inhaled) for example derived from a measurement of the flow rate of the inhaled gas mix, ambient pressure, an estimation or measurement of the user's blood volume, etc. In some embodiments, an index of user dO2 levels may be constructed for reference.

Other user body parameters may be used, for example and without limitation, parameters related to the user's weight/height, age and/or physical fitness.

In some embodiments, the monitoring systems and methods described herein may further be used to derive a cognition level or index of the user at different levels of blood oxygenation (bounded to hemoglobin and/or dissolved in blood or tissues). The cognition level may include characterizations of user fatigue, stress, confusion, engagement, workload and may be used to assess the ability of the user to concentrate and/or accomplish different tasks (e.g. efficiency and precision), such as diving, piloting an aircraft or spacecraft, etc. The systems and methods described herein, in some embodiments, may further display the user's cognition level in addition to health-related risks of hyperoxia and/or hypoxia. The cognition level may be derived, for example, by initially assessing the user's ability to execute specific tasks (i.e. speed of execution, number of errors, etc.) while monitoring changes in blood oxygen levels and deriving correlations from those measurements. In the case where the user's cognitive level is determined to be below a certain safety threshold for performing a specific task (i.e. flying an aircraft, etc.), the user may decide or be forced to stop and/or take a break.

With reference to FIG. 1, and in accordance with one exemplary embodiment, a blood oxygen monitoring system, such as a cerebral blood oxygen monitoring system, generally referred to using the numeral 100, is shown. In FIG. 1, the illustrated physical activity is scuba diving or deep diving. As noted above, while scuba diving or deep diving is provided herein as an example, other activities may be considered to benefit from the features, functions and advantages of the herein-described embodiments without departing from the general scope and nature of the present disclosure.

In the illustrated embodiment, the system 100 is configured to monitor for abnormal cerebral blood oxygenation levels of the diver underwater. In this exemplary embodiment, the diver uses a closed or semi-closed circuit rebreather device 102, though other oxygen-providing devices or means may be considered, for example, where a recycling of exhaled gases is not applied. As mentioned above, using such devices at great depths can lead to an increased partial oxygen pressure which itself may result in the onset of hyperoxia.

In this embodiment, the system 100 generally comprises at least one near-infrared spectroscopy (NIRS) probe 104 fixable to the user's head for acquiring cerebral blood oxygenation data representative of at least deoxyhemoglobin levels over time. As mentioned above, other embodiments may be configured to monitor different/additional chromophore molecules present in the blood, such as oxygenated haemoglobin levels, without limitation.

In some embodiments, this at least one NIRS probe 104 may be integrated inside a type of headwear, such as a headband or cap. In this case, the headwear should be solidly affixed on the head of the user to avoid suboptimal measurements due to a suboptimal contact between the NIRS probes and the user's skin, water contamination or the like.

As will be discussed below, other embodiments may use different skin contact locations, for example and without limitation, the neck region.

From the absorption spectra measured from this at least one NIRS probe, a relative cerebral (or regional) blood levels of these proteins may be calculated. To do so, the at least one NIRS probe 104 is operatively connected to a digital data processor 106 programmed to compute the relative concentrations of both O2Hb and HHb, and/or a change in molar concentration of HHb or similar. In this embodiment, data is transferred through a wired connection 108, but other embodiments, such as wireless connections, may also be employed. As will be explained in more detail below, the digital data processor 106 is further programmed to use these relative concentration measurements to derive or define at least a lower or higher health risk rating of hyperoxia, and/or other oxygenation health-related ratings, such as related to hypoxia, for example.

It will be appreciated that the processor 106 may take various forms, which may include, but is not limited to, a dedicated computing or digital processing device, microprocessor, a general computing device, tablet and/or smartphone interface/application, and/or other computing device as may be readily appreciated by the skilled artisan, that includes a digital interface to a at least one NIRS probe output so to acquire and ultimately process readings/spectra captured thereby.

Furthermore, the embodiment of FIG. 1 further comprises a digital user interface 110 capable of displaying a health risk indicator to the user obtained via the digital data processor 106. As shown in the embodiment of FIG. 1, both the digital data processor 106 and the digital user interface may be contained inside the same water-tight device, here a watch-like device worn on the wrist using a strap 112. In other embodiments, the digital user interface 110 and digital data processor 106 may also be separated from each and communicatively linked to each other and to the at least one NIRS probe via a wired or wireless connection. In some embodiments, the digital user interface may be comprised of a computer with a digital display screen, tablet, smartphone application or like general computing device, or again a dedicated device having a graphical or like general computing device. In some embodiments, the digital user interface may comprise a heads-up display located inside a mask, goggles and/or glasses (not shown).

In some embodiments, additional sensors may also be used in parallel with the at least one NIRS probe 104. For example, pressure, temperature sensors (and/or one or more same and/or distinct physiological sensors or like components operable to interface with the user (e.g. via a direct or indirect user contact, such as a skin contact or like interface operable in contact with or in close proximity to the user's skin or body) may also be used to acquire environmental and/or physiological signals and operatively connected to the digital data processor 106, either for direct transmission to the digital user interface 110 or to be used as additional input in the determination of the user's higher or lower health risk rating of hyperoxia, hypoxia, etc. Examples of physiological signals that may be monitored via one or more physiological sensor include, without limitation, electrocardiograms (ECG), electroencephalograms (EEG), breathing rate, VO2, blood pressure, body temperature, etc. As will be discussed below, in some embodiments, one or more physiological signal may be correlated with the NIRS probe signal to provide a more precise quantification of blood oxygen levels.

In some embodiments, user body position may also be monitored with one or more accelerometers (not shown), as the user body position affects the flow of blood to the head region (as will be explained below) and thus the spectral response. Therefore, in some embodiments, system 100 may further comprise one or more accelerometers communicatively linked to digital data processor 106 to detect changes in user body position or orientation (e.g. sitting or supine).

In some embodiments, system 100 may further comprise an internal memory or data storage module (not shown) communicatively linked to digital data processor 106 to store additional data which may be used to improve the monitoring capabilities of system 100. For example, and without limitation, a spectral database comprising information about the spectral signature of one or more known chromophores may be stored therein.

In some embodiments, digital data processor 106 may further be configured to provide additional features, such as an artificial-intelligence-based monitoring system (not shown). In some embodiments, digital data processor may be configured to run an artificial intelligence program to provide user-specific automated or semi-automated oxygen monitoring, as will be explained below.

Furthermore, digital data processor 106 may also, in some embodiments, be communicatively linked to the oxygen providing apparatus/device 102 so as to regulate the flow of gas to the user, depending on the user's blood oxygen levels being monitored.

Figure 2:
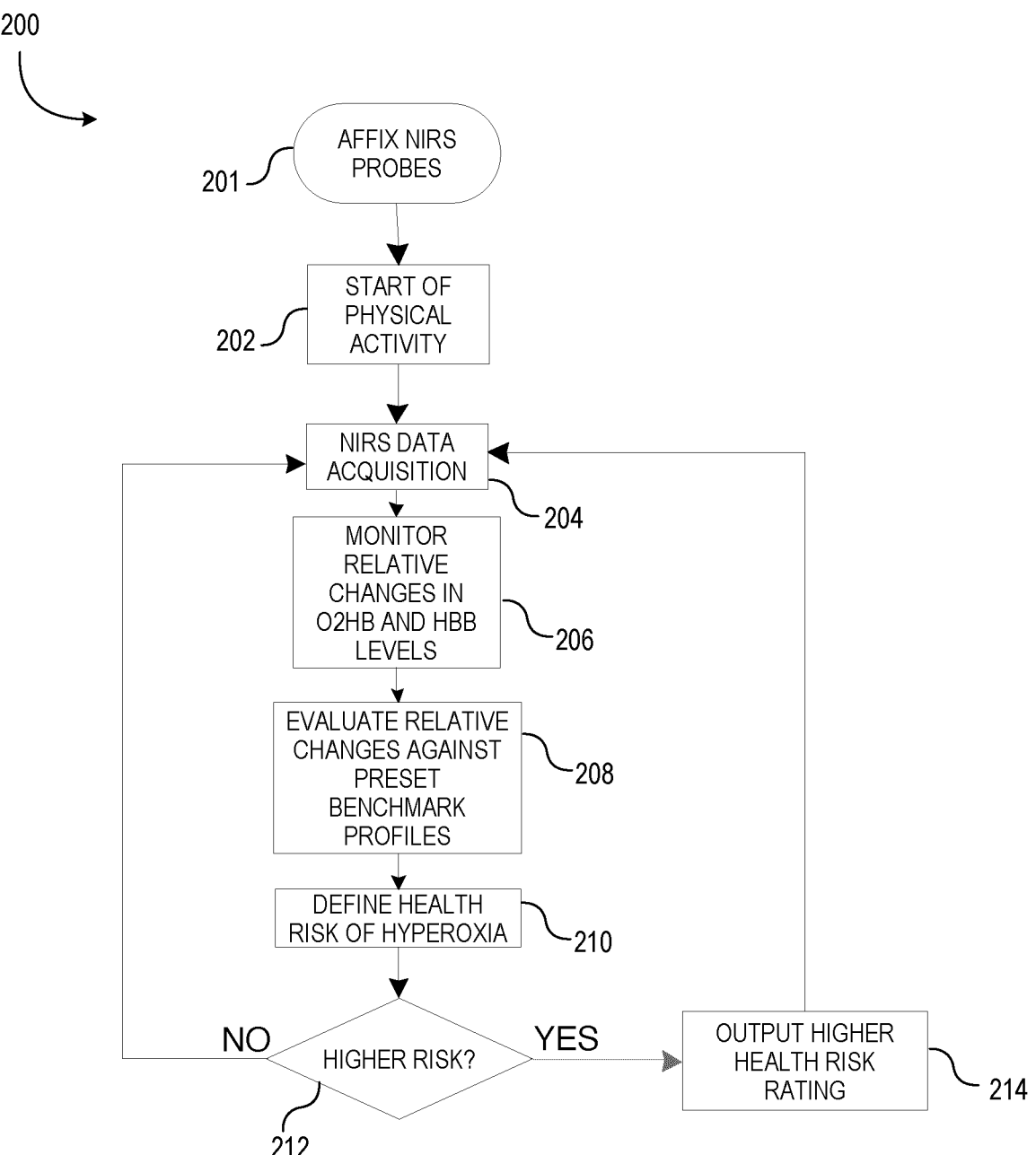
FIG. 2 is a diagram of a monitoring method for abnormal cerebral blood oxygenation levels of a user partaking in a physical activity requiring the use of an oxygen providing apparatus, in accordance with one embodiment.

With reference to FIG. 2 and in accordance with one exemplary embodiment, a method for deriving a health indicator from measurements taken using the at least one NIRS probe will now be described for a user partaking in an activity requiring the use of an oxygen providing apparatus. The user first affixes (step 201) at least one near-infrared spectroscopy (NIRS) probe to, for example, his/her head. As explained above, the at least one probe may be integrated within a form of headwear, although generally any wearable user body location may be used. Non-limiting examples of suitable wearable monitoring device comprising one or more probes may include, but are not limited to, a wristband, wristwatch, bracelet, necklace, ring, belt, glasses, clothing, hat, anklet, headband, chest harness, patch, skin probe to name a few, or any other wearable item location that is capable of obtaining a NIRS signal.

The user then starts partaking in any activity (such as a physical activity or other) as usual (step 202) while the at least one probe acquires data relative to his/her oxyhemoglobin (O2Hb), deoxyhemoglobin levels (HHb) or other chromophore levels as mentioned above (step 204). This data acquisition is done continuously, in real-time or at short intervals. In the presently discussed embodiment, the acquired data is analyzed by monitoring for relative changes in O2Hb and HHb levels (step 206). These relative changes are automatically evaluated against present variations corresponding to a plurality of benchmark cerebral blood oxygenation profiles (step 208). These profiles are determined beforehand and programmed, for example, into the digital data processor 106 as explained above. As mentioned above, the profile may further comprise, in some embodiments, data related to one or more physiological signals, which would be acquired concurrently using one or more physiological sensors. Furthermore, as discussed before, The profile themselves are associated with a preset blood oxygenation index that defines at least a lower health risk rating and a higher health risk rating of hyperoxia (step 210) and/or other oxygenation health-related characteristics.

As mentioned above, method 200 may also use at step 210 an artificial-intelligence-based system to provide an improved monitoring capabilities of the user's oxygen levels and related risks of hyperoxia/hypoxia. Such a system may receive and analyze in real-time any data being acquired via the NIRS probe, one or more physiological sensors, user-body parameters, total oxygen intake, manual changes in the oxygen content flow rates, etc. Different AI, machine learning and/or system automation techniques may be considered to implement such a program. For example, these may include, without limitation, supervised and/or unsupervised machine learning techniques, linear and/or non-linear regression, decision trees, etc. Deep learning algorithms may also be used, including but not limited to, neural networks such as recurrent neural networks, recursive neural networks, feed-forward neural networks, convolutional neural networks, deep-belief networks, multi-layer perceptrons, self-organizing maps, deep Boltzmann machines, and stacked de-noising auto-encoders or similar. As such, the intelligent monitoring features may operate autonomously or semi-autonomously, with limited or without explicit user intervention.

Using hyperoxia as an example, if the method determines at step 212 that the user is experiencing a lower risk of hyperoxia, nothing is done and the method continues the process of acquiring data of step 204. In contrast, if the method determines that the user is currently experiencing a higher health risk of hyperoxia, the method then outputs the higher health risk rating to the user (step 214) to inform him/her of the higher risk so that he/she may take action to reduce it. Different examples of indicators may include, but are not limited to, visible indicators such as flashing and/or coloured lights, audible alerts (e.g. relayed through a communicatively-linked earpiece), vibratory device, or the like, which may take the form of continuous, blinking, pulsing, rhythmic, periodic and/or escalating alerts indicators. In some embodiments, visual indicators may be shown on a digital display or a heads-up display, as mentioned above.

Then, as in the previous case, the method continues the process of acquiring data (step 204). The paragraphs below will explain, in part, how the cerebral blood oxygenation profiles may be determined.

Figure 3:
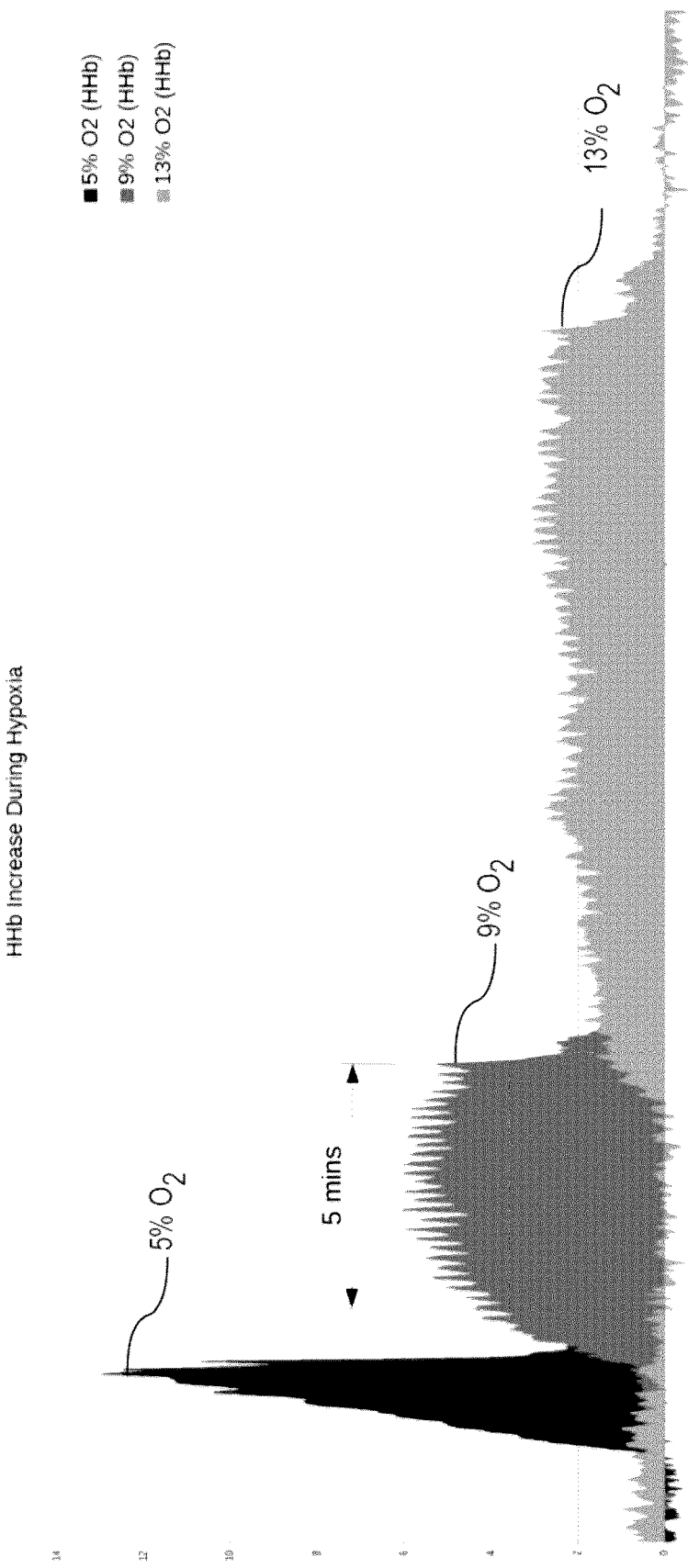
FIG. 3 is an exemplary plot of the change in time of the relative absorbance of deoxyhemoglobin as measured by NIRS of an individual breathing a series of different gas mixtures containing lower than normal concentrations of oxygen (hypoxic mix), in accordance with one embodiment.

With reference to FIG. 3, and in accordance with one exemplary embodiment, a plot is provided of the relative change in cerebral deoxyhemoglobin (HHb) absorbance (e.g. optical density), as a function of time, of an individual breathing a series of gas mixtures with a reduced oxygen concentration (hypoxic mixes). The measurements were taken using a commercially available NIRS system developed by Artinis Medical Systems B.V. The absorbance values are relative to the baseline values obtained with the same individual breathing normal air (21% $O_2$) and three runs were measured with hypoxic mixes of 5%, 9% and 13% oxygen respectively. For each data series, the individual sustained breathing the associated mix as long as comfortable, then returned to breathing normal air again. Clearly, breathing lower levels of oxygen, as is well known, leads to a rapid increase in HHb levels. The lower the oxygen level, the faster and higher the rise in measured HHb levels is observed and the shorter the time the individual could sustain respiration.

Figure 4:
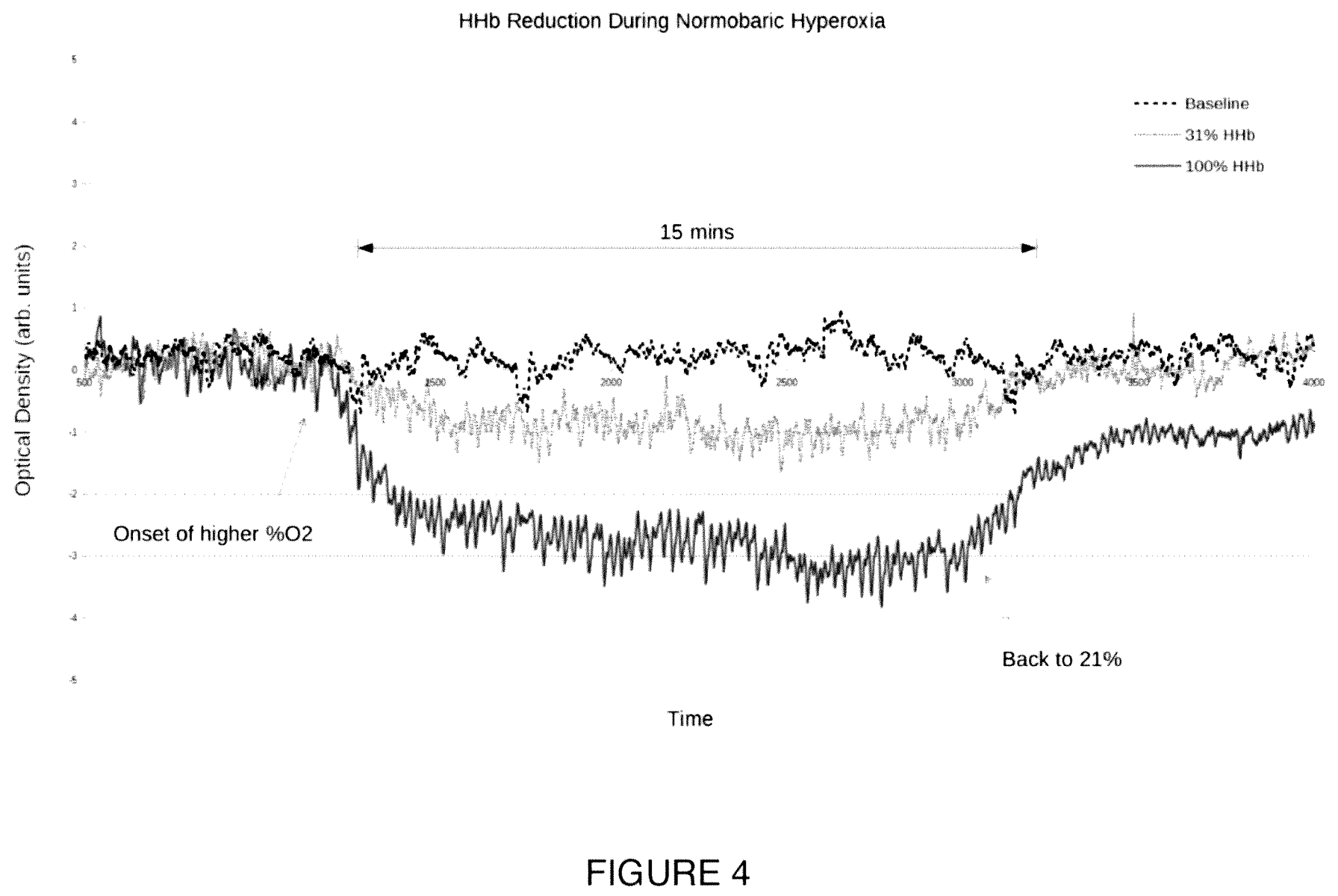

In contrast to FIG. 3, FIG. 4 is a plot, as a function of time, of the change of HHb levels while breathing an increased concentration of $O_2$ (hyperoxic mix). Three measurements are shown, one baseline measurement at a normal $O_2$ concentration of 21% (e.g. normal air) (dark gray dotted line), one measurement done with a mix containing 31% $O_2$ (light gray dotted line) and one measurement with pure $O_2$ (black line). In the last two measurement series, the individual was breathing normal air in the first and last 5 minutes of the experiment. We clearly see the reduction in HHb concentration measured with the increased intake in $O_2$. Moreover, while the measurements at 31% $O_2$ show a quick return to the baseline value after the individual stopped breathing the gas mixture, in the second case, while the HHb concentration increases and stabilizes after the pure $O_2$ is removed, it never quite returns to baseline during the acquisition time, though will clearly eventually return to baseline over time. These measures thus illustrate the tissue's ability to store oxygen, which may become increasingly important for greater oxygen partial pressures. Using methods as described herein, in some embodiments, means may thus be provided to monitor the discharge of oxygen from tissues into the blood.

Figure 5:
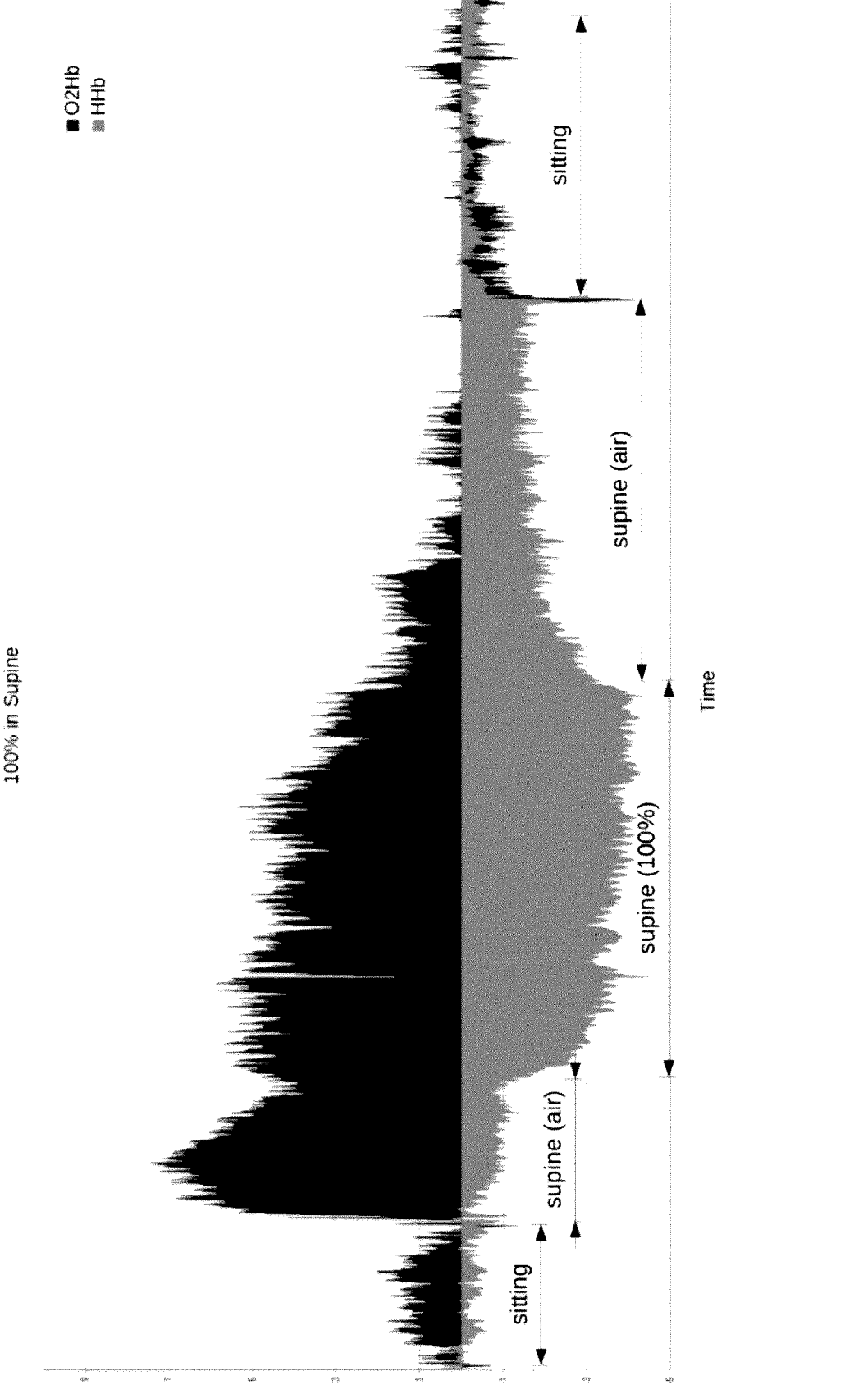
FIG. 5 is an exemplary plot of the change in time of the relative absorbance of both oxyhemoglobin and deoxyhemoglobin as measured by NIRS of an individual breathing normal air, an hyperoxic mix and normal air again, while changing position from a sitting position, a supine position and a sitting position again, in accordance with one embodiment.

FIG. 5 shows the effect, as a function of time, of both changing an individual's position (sitting or supine) and breathing pure oxygen (100% $O_2$) vs. normal air (21% $O_2$). Both the relative absorbance values of the oxyhemoglobin (O2Hb) and HHb are shown. For this experiment, the individual is initially breathing normal air (21% $O_2$) in a sitting position for 5 minutes, followed by being put in a supine position for another 5 minutes. The individual, still in a supine position, was then exposed to a pure oxygen gas via a face mask for a number of minutes. Without changing the individual's position, the mask was then removed, allowing the individual to breath normal air again. Finally, after waiting a few minutes, the individual was allowed to sit again. We clearly see the effects these changes have on both the O2Hb and HHb measurements. However, we find that the O2Hb and HHb responses are not symmetrical, indicating that measurement only the O2Hb concentration may be unreliable as the only indicator of cerebral blood oxygenation in all contexts. However, a careful measurement of both O2Hb and HHb concentrations using NIRS does lead to the determination of a more precise index.

FIGS. 3 to 5 clearly show characteristic signatures of the changes in O2Hb and HHb levels not only as a function of oxygen content breathed by an individual but also as a function of the individual's relative position. By measuring the changes in O2Hb and HHb levels for a series of different oxygen levels in different individuals, a series of benchmark cerebral blood oxygenation profiles may be recorded. These profiles may then be digitally associated with a preset cerebral blood oxygenation index that may then be used to associate a lower or higher risk rating of hyperoxia in the individual, of example. The benchmark profiles may be expanded to include different partial oxygen pressures by doing measurements inside a hyperbaric or isobaric chamber, for example.

Figure 10:
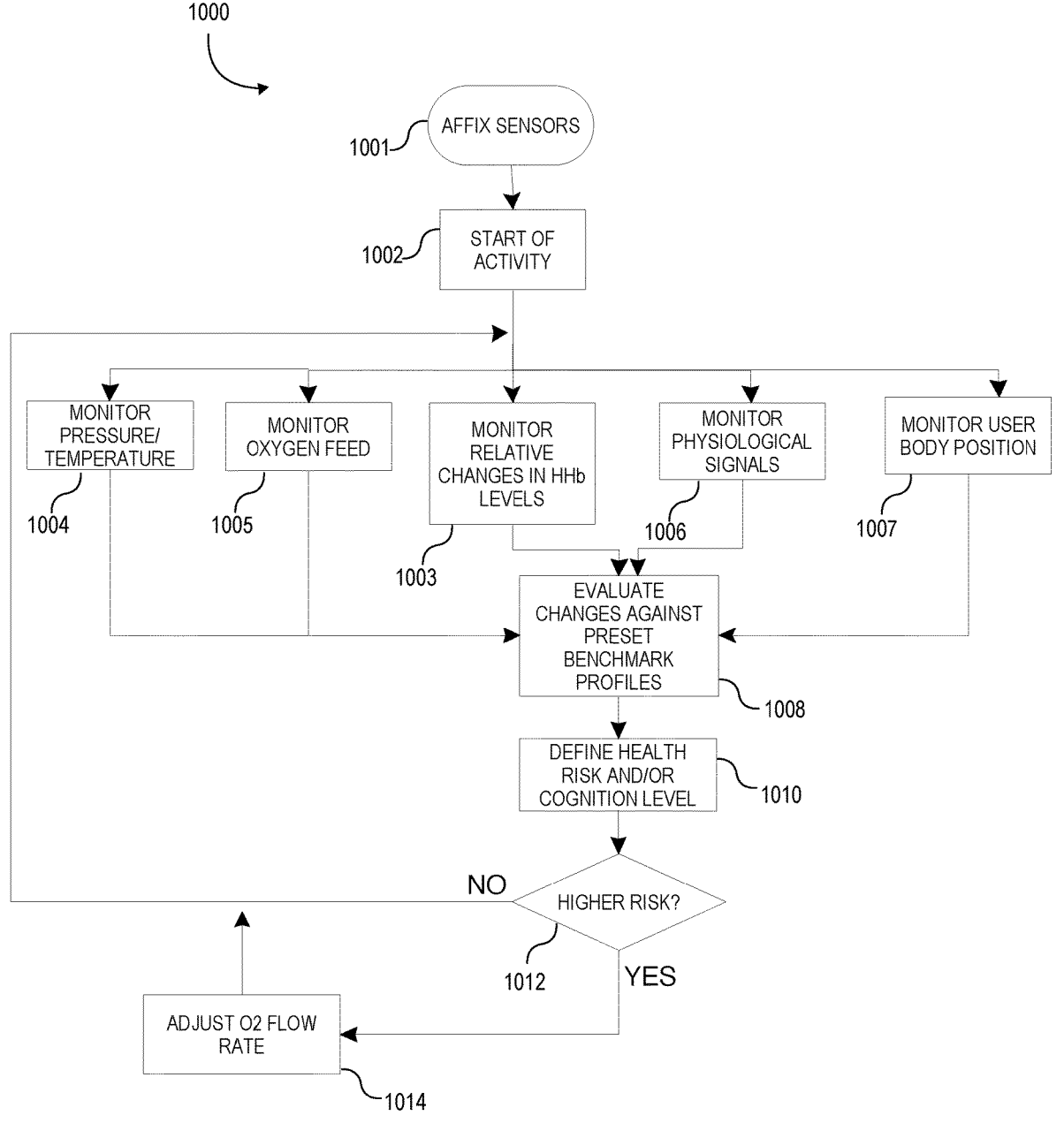
FIG. 10 shows a diagram of another method for monitoring a user's health risk for a user partaking in an activity requiring the use of an oxygen providing apparatus and/or inside a sealed pressurized environment, in accordance with one embodiment.

With reference to FIG. 10 and in accordance with one exemplary embodiment, another method for monitoring a user's health risk when partaking in an activity requiring the use of an oxygen providing apparatus and/or inside a sealed pressurized environment, generally referred to using the numeral 1000, will now be described. Similar to the embodiment described in FIG. 2, at step 1001 one or more sensors are affixed or put in contact with the user's skin at one or more locations. These sensors may be integrated into a wearable device as explained above. Once the user begins the activity at step 1002, method 1000 immediately starts monitoring one or more parameters. At step 1003, the method monitors via one or more NIRS probes the molar concentration of HHb in the user's blood (for example in the cerebral region), but may also optionally monitor in parallel other parameters such as ambient pressure and/or tempera-
ture (step 1004), oxygen intake (step 1005), one or more
physiological signals via one or more physiological sensors
(step 1006) and/or user body position via one or more
accelerometers (step 1007). Data acquired from steps 1003
to 1007 is sent to a central processing unit (i.e. digital
processing unit 106 for example) to be analyzed and com-
pared to preset benchmark profiles at step 1008. As dis-
cussed above, in some embodiments, step 1008 may be
performed using machine-learning techniques such as deep
learning techniques or similar. From this analysis, a health-
related risk of hyperoxia/hypoxia and optionally a user
cognition level may be defined at step 1010. At step 1012,
these risk and/or cognition levels may be compared to
previous levels to determine if an increase in risk or a loss
of cognition has occurred. In this case, method 1000 may
automatically adjust the flow of oxygen delivered to the user
to reduce the risk and/or increase the cognition level.
Optionally, at step 1014 a warning may also be delivered to
the user as explained above. The method then goes back to
monitoring different parameters (steps 1003 to step 1007) to
assess a new risk and/or cognition level.

With reference to FIGS. 6 to 9, and in accordance with
one exemplary embodiment, different plots are provided of
the change in cerebral HHb concentration (in μM or $10^{-6}$
mol/L), as a function of time, of an individual subjected to
different oxygen partial pressures. These figures clearly
show the different correlations between the measured molar
concentration of HHg different parameters, including partial
oxygen pressure but also sustained physical activity. The
measurements were again taken using a commercially avail-
able NIRS system developed by Artinis Medical Systems B.
V. Changes in molar cerebral HHb concentrations were
calculated from changes the NIRS attenuation signal using
the light diffusion model of Suzuki et al. mentioned above.
Thus, in FIGS. 6 to 9, only changes in the measured cerebral
HHg concentration with respect to the initial value are
meaningful and the initial concentration value at the start of
each Figure is arbitrary.

Figure 6:
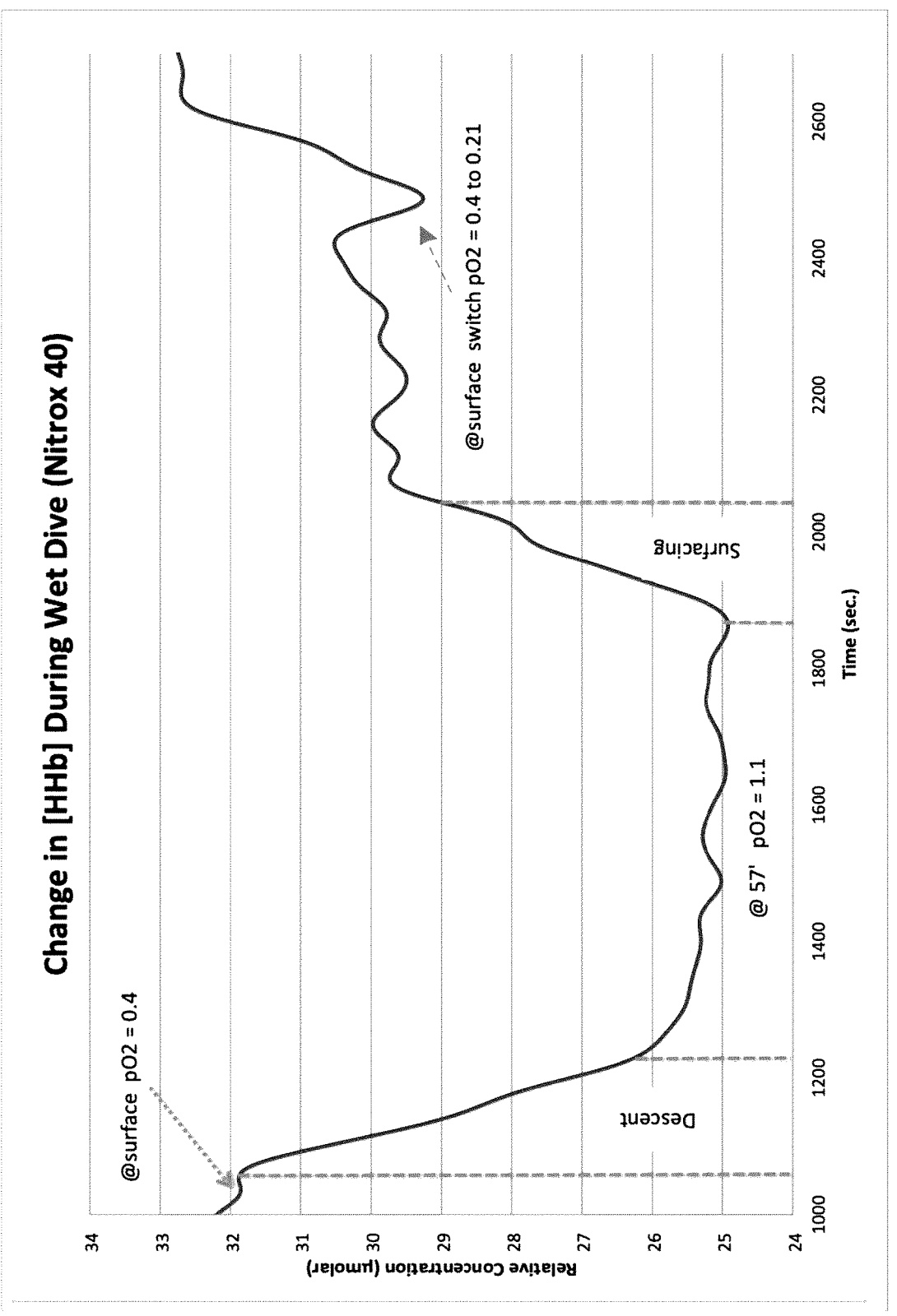
FIG. 6 is an exemplary plot of the change in time of the relative molar concentration of cerebral deoxyhemoglobin as measured by NIRS of an individual breathing different gas mixtures and immersed in water at different depths, in accordance with one embodiment.

For example, FIG. 6 shows a plot of an individual being
completely immersed in water at different depths and breath-
ing sequentially from two different gas mixtures (normal air
and Nitrox 40 hyperoxic mix). At the start of the plot shown
in FIG. 6, the individual is breathing the Nitrox 40 mix while
floating at the surface (e.g. p02=0.4). As the depth increases,
we clearly see the concentration of cerebral HHb decreasing
as well with respect to the initial value (at the surface at
t=2000 sec.) by about 7 μM until a depth of 57 feet is
reached with a corresponding partial oxygen pressure of 1.1.
The diver stayed at that depth for about 10 minutes before
resurfacing at around 2400 sec., where we see the concen-
tration of HHb increasing correspondingly by about 2.5 μM,
returning it close to its initial value at the start of the
experiment. Thus FIG. 6 shows a clear correlation between
changes in oxygen partial pressure and corresponding
changes in cerebral HHb concentration.

Figure 7:
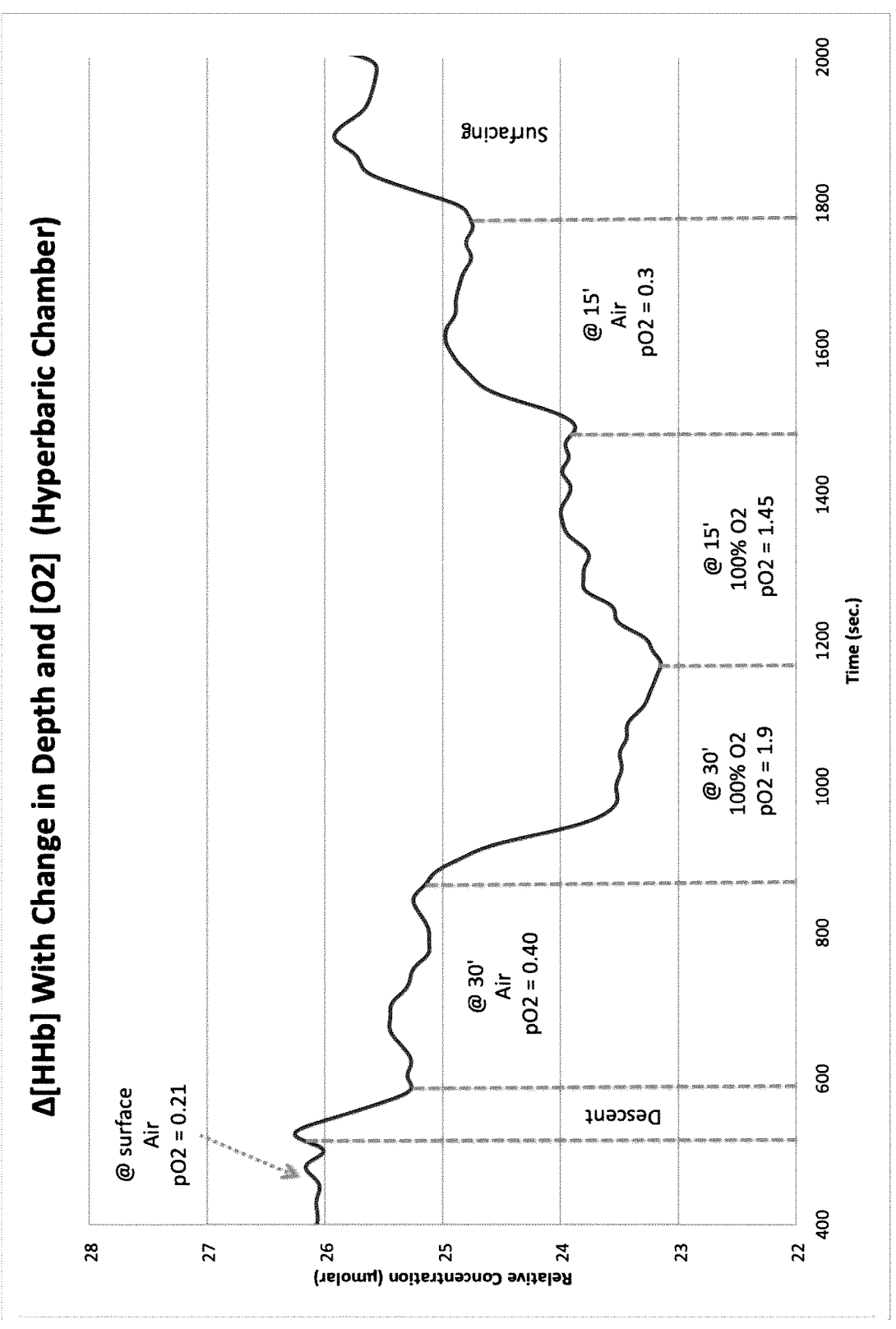
FIG. 7 is an exemplary plot of the relative change in concentration of cerebral deoxyhemoglobin as measured by NIRS of an individual breathing different gas mixtures inside a hyperbaric chamber, in accordance with one embodiment.

Similarly, FIG. 7 shows a plot of the change in cerebral
HHb concentration as a function of time but for an indi-
vidual inside a sealed hyperbaric chamber where both a
change of O2 concentration was administered and a change
in depth simulated by varying the pressure. Thus, the partial
oxygen pressure inside the user could be changed by either
changing the pressure in the chamber or by changing the
oxygen concentration the individual was breathing (air or
hyperoxic mix). Starting from a normal oxygen partial
pressure of 0.21 (e.g. breathing normal air at atmospheric
pressure), the pressure inside the chamber was increased to simulate a corresponding depth of 30 feet (pO2=0.40) which
led to a small decrease in cerebral HHb concentration (with
respect to its initial value at t=400 sec.) of about 0.8 μM.
Then, at around 900 seconds, the pressure was kept constant
but the breathing mix was changed from air to pure oxygen
(pO2=1.9). We quickly see the HHb concentration further
decreasing by a value of about 2 μM. The next step consisted
of letting the individual breathe pure oxygen but to decrease
the pressure to simulate a depth of 15 feet (pO2=1.45). We
see that this leads to a corresponding increase of the HHb
concentration by about 0.8 μM. Then, keeping the pressure
constant, the individual was given normal air to breathe
(p.02=0.3). We again find a corresponding rapid increase in
the concentration of cerebral HHb by a value of 1 μM.
Finally, the normal atmospheric pressure was restored which
led the concentration to return to its initial value (at t=0).
Thus, we clearly see in FIG. 7 the correlation between
changes in depth and partial oxygen pressure and the cor-
responding variations in the cerebral HHb concentrations.

Figure 8:
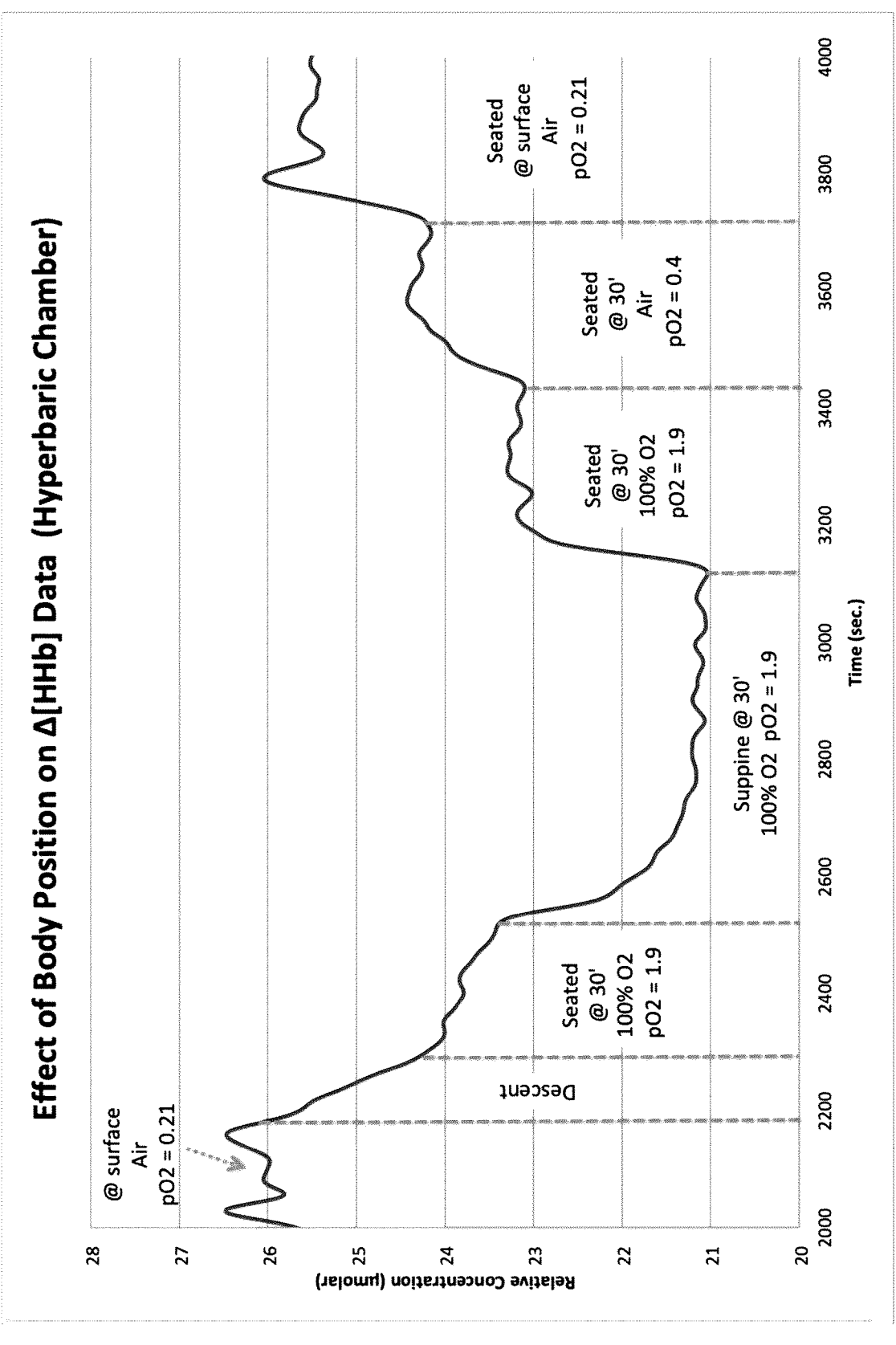
FIG. 8 is an exemplary plot of the relative change in time of the concentration of cerebral deoxyhemoglobin as measured by NIRS of an individual both changing positions (sitting or supine) and breathing different gas mixtures inside a hyperbaric chamber, in accordance with one embodiment.

FIG. 8 illustrates, similarly to FIG. 5, the effect, as a
function of time, of both changing an individual's position
(sitting or supine) and breathing pure oxygen (100% O2) vs.
normal air (21% O2), again inside a hyperbaric chamber. In
the plot of FIG. 8, the individual is first in a seated position
while breathing normal air. The pressure was then increased
to a corresponding depth of 30 feet, resulting in a corre-
sponding decrease in the HHg concentration by about 2 μM
with respect to its initial value (t=2000 sec.). Then, the
individual, still seated, was administered pure oxygen
(pO2=1.9) which leads to another decrease of the HHg
concentration by about 0.6 μM. Next, keeping the pressure
constant (30 feet) and still breathing pure oxygen, the
individual was asked to take to a supine position, which
causes the measured concentration of cerebral HHb to
decrease further by about 2 μM. Going back to a seated
position cancelled, as expected, the previous variation by
increasing the HHg concentration by 2 μM. Now changing
the breathing mix from pure oxygen to normal air (but
keeping the pressure constant and a seated position) also
returned the cerebral HHg concentration to a value of about
1.9 μM below the initial value. Finally, decreasing the
pressure to normal atmospheric pressure returned the mea-
sured HHg concentration close to the initial value at the start
of the experiment. Thus, we see that the derived molar
concentration also correlates well with the user body posi-
tion.

Figure 9:
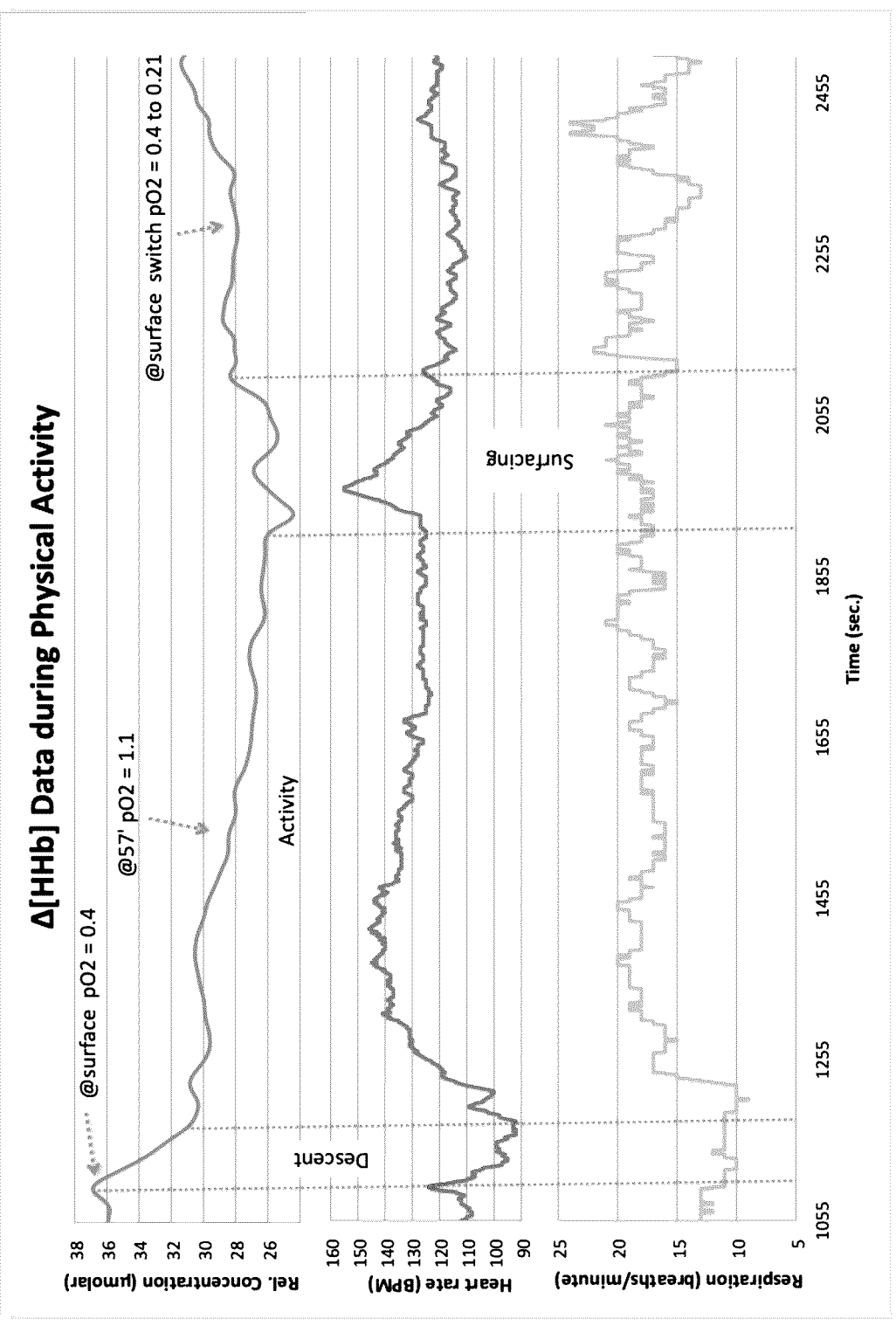
FIG. 9 shows three exemplary plots illustrating the relative change over time in the concentration of cerebral deoxyhemoglobin; the heart rate and the breathing or respiration rate, from top to bottom respectively, of a user engaging in an underwater physical activity as a function of time, in accordance with one embodiment.

As mentioned above, in some embodiments, one or more
physiological signals may be acquired concurrently with the
NIRS signal to provide an increased accuracy in the calcu-
lated blood oxygen content, for example by using measured
correlations between the changes in these one or more
physiological signals and the HHb concentration levels (or
other chromophores) when the user is engaging in a physical
activity. For example, in FIG. 9 we see three plots illustrat-
ing the corresponding change over time of the concentration
of cerebral HHb, the user's heart rate (in beat per minute or
BPM) and the breathing or respiration rate (in breaths per
minute), from top to bottom respectively, of a user engaging
in an underwater physical activity as a function of time. In
FIG. 9, the individual is initially breathing an hyperoxic mix
(pO2=0.4) while at rest at the surface and then descends
underwater to a depth of 57 feet (pO2=1.1), leading to a
corresponding decrease in the measured cerebral HHb con-
centration of about 5 μM below the initial value (t=1055
sec.). This decrease is also correlated with a small decrease
in the heart rate from 120 BPM to about 95 BPM. The
individual then started engaging in a physical activity for more than 10 minutes, which immediately results in an increase in the measured heart rate (from 95 BPM to about 128 BPM with peak at 140) and the respiration rate (from about 10 breaths per minutes to around 19-20 breaths per minute), and a corresponding decrease of the HHb concentration by about 4 µM (e.g. 10 µM below the initial value). This decrease in the HHg concentration is directly linked to the physiological processes caused by the physical activity being performed and not linked to the partial oxygen pressure alone, as will be seen below. Following this, the individual returns to the surface while still breathing the hyperoxic mix, which shows as a slight increase in the HHb concentration by a value of about 4 µM. Finally, the diver resumes breathing normal air, which shows up again as an increase in the HHb concentration of about 4 µM. Thus, the measured cerebral HHg concentration at the end is still 4 µM below the initial value at the start of the experiment, which roughly corresponds to the decrease observed when the user was engaged in the physical activity, as expected.

As introduced above, in some embodiments, oximetry data can be acquired using a spectroximetry probe, such as that described in greater detail below. For example, the systems and methods described herein provide, in accordance with different embodiments, different examples of a system and method for monitoring or assessing one or more physiological or health-related parameters or condition(s) in a user or patient via full or broad-spectrum oximetry, which is herein interchangeably referred to as spectroximetry or hyperspectral oximetry. Using a spectroximetry probe as described below can, in some embodiments, further enhance implementation of a physiology assisted dive profiling model, as described above, though other oximetry probes may also be considered in that context. Meanwhile, a spectroximetry probe and system as described herein may provide other benefits in other contexts, as detailed below, without limitation to physiology adaptive profiling.

In contrast with standard oximetry, full or broad spectrum oximetry (spectroximetry or hyperspectral oximetry), as provided by the exemplary systems and methods described below, in accordance with different embodiments, has the unique feature of allowing the measurement of the entire absorption spectrum of interest, such as for example between 600 nm and 1000 nm. Namely, a broad range of probing wavelengths can be leveraged, in different embodiments, to extract a coarse or even fine resolution absorption spectrum that carries a greater wealth of information for the purposes of conducing and outputting a more detailed analysis and evaluation of the probed tissue's oxygenation profile, status or condition.

For instance, in some embodiments, spectroximetry has the advantage of measuring absolute energetic transmission over a broad range of wavelength. This absolute measurement can allow for the comparison of absorption profile variations for the same patient at different times, and between patients, for example. Current oximetry methodologies rely on indices that do not lend to such analysis.

Figure 11:
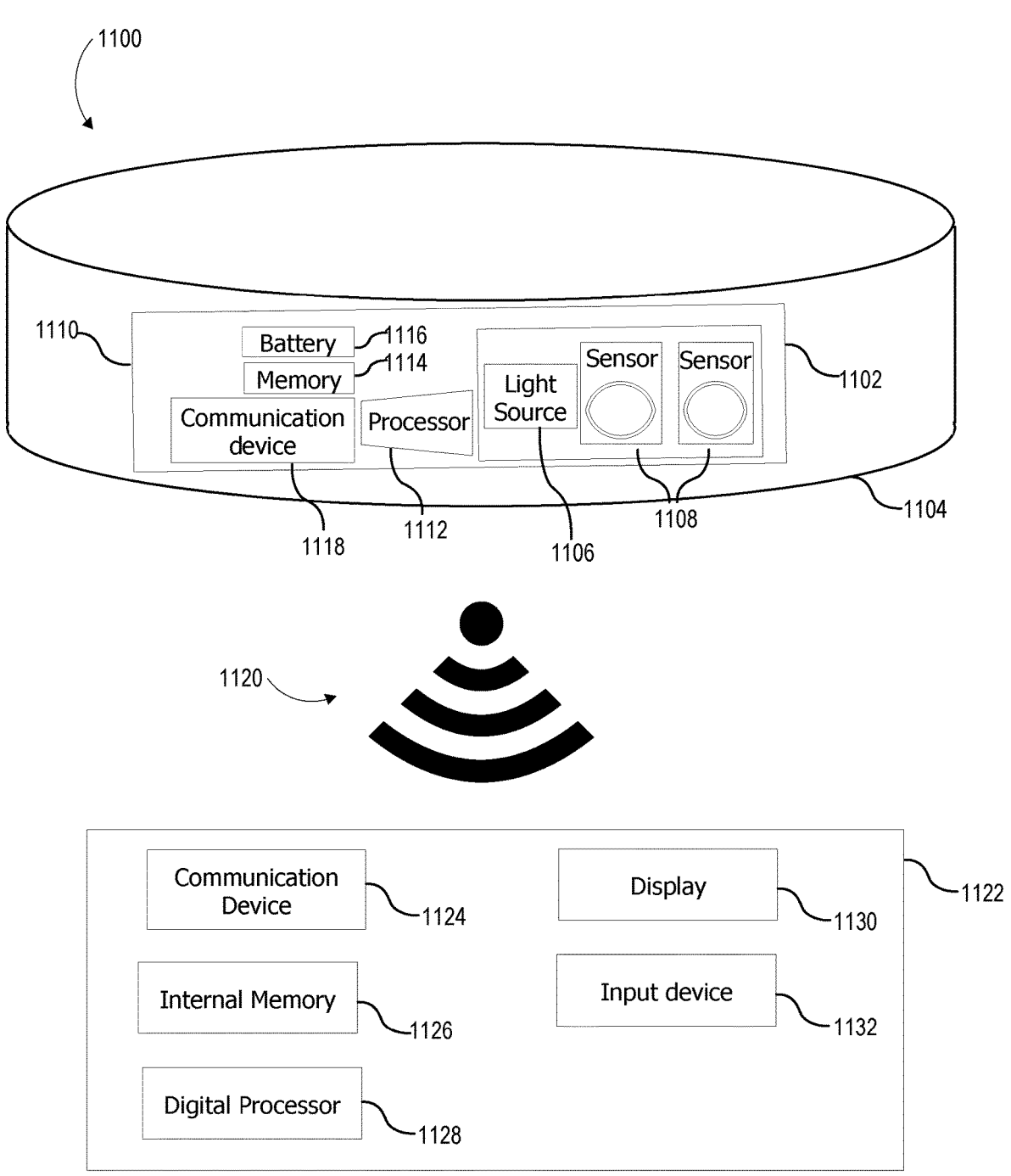
FIG. 11 is a schematic diagram of a broad or full spectrum oximetry (spectroximetry) system, in accordance with one embodiment.

With reference to FIG. 11, and in accordance with one exemplary embodiment, a full spectrum oximetry system, interchangeably referred to as a spectroximetry system, and generally referred to using the numeral 1100, will now be described.

In this exemplary embodiment, system 1100 comprises a broad-spectrum probe 1102, which may be attached to the skin above the tissue of interest or as illustrated herein integrated into or inside a type of headwear (here headband 1104). Probe 1102 generally comprises at least one broad-spectrum infrared light source 1106, for example one or more LEDs may be used alone or in combination to generate IR light covering a broad range of the infrared spectrum (e.g. for example wavelengths between 600 nm to 1000 nm). Light source 1106 is generally configured so as to emit light into the tissue of interest, this example the head/brain region. It some embodiments, it may comprise one or more LEDs manufacture into a single device, or in other embodiments multiple LEDs may be used at different physical locations. Naturally, while a broad IR range of 600 nm to 1000 nm is presented here as an example, it will be appreciated upon further reading that different shorter or longer ranges can be considered without departing from the general scope and nature of the present disclosure. It will also be appreciated that different light sources and/or combinations of light sources 1106 may be considered to provide such range, to accommodate different probing spectrum intensity or continuity profiles, or the like, without departing from the general scope and nature of the present disclosure. Furthermore, while focus is made on a broad spectrum IR light source, other complementary spectral regions may also be considered where absorption, transmission and/or reflectance spectra can provide complementary information or characteristics on blood-oxygen or other blood-constituent elements of interest.

In this embodiment, probe 1102 further comprises at least one high-resolution miniature spectrometer or sensor 1108 to record one or more high-resolution absorption or transmission spectra of the transmitted or reflected light from light source 106. Miniature spectrometer 1108 may take different forms and/or have different specifications. In general, spectrometer 1108 should have a high spectral resolution sufficient to confidently reproduce a representative spectral signature received by probe 1102 over the broadband infrared range of interest. In some embodiments, spectrometer 1108 may be based on a diffraction grating design, a multi-layer filter design, a combination thereof or another design entirely. For example, and without limitation, spectrometer 1108 may be operable to acquire spectral data with a 5 nm resolution over the whole range between 600 nm to 1000 nm (e.g. 10, 40 or even 80 distinct wavelengths/ spectral regions). The skilled technician will understand that different numbers of wavelengths with different resolutions may be considered. In general, the acquired spectral data should have a resolution that allows to differentiate between different peaks or dips of interests, with sufficient details so as to allow for comparative analysis of such acquired spectra with designated representative spectra or spectral variations therein, and or with previously or continuously acquired spectra as a user's condition and/or environment changes. Namely, as will be detailed below, acquired spectra may be used for comparative analysis as a single diagnostic or screening tool against preset or designated standard spectra representative of healthy, low risk or high risk conditions, illnesses, and/or environmental scenarios, or again as continuous or regular monitoring means whereby observed spectral profile variations in different spectral regions or combinations of such regions can be quantitatively or qualitative mapped to corresponding conditions or risk factors.

With continued reference to FIG. 11, different configurations of light source 106 and spectrometer 1108 may be considered for probe 1102. In some embodiments, a single light source 1106 and spectrometer 108 may be used. For example, a single broad IR spectrum LED and a single sensor may be used, with a pre-defined distance therebetween. In some embodiments, sensor 1108 and the single LED of light source 1106 may be placed opposite each other (e.g. with the tissue of interest in-between) so as to measure the transmission (or absorption) spectra. In other embodiments, a linear configuration may be used where the LED of light source 1106 and sensor 1108 are placed next to each other (as shown in FIG. 11), pointing in the same direction, in order to measure the light scattered back from the tissue volume they are placed on.

In yet another embodiment, one sensor/spectrometer 1108 may be placed linearly alongside a light source 1106 comprising multiple LEDs (reflection-type design). In this configuration it may be possible to have different pre-defined distances between each LED and sensor 1108. The difference in distances may thus allow for spatially-resolved data to be acquired.

In yet another embodiment, probe 1102 may consist of a light source 106 comprising a single LED, but with sensor 1108 comprising several individual sensors instead of a single device, e.g. laid out in a linear spatially-resolved reflection-type configuration. This layout thus also allows spatially-resolved spectrometric data with different pre-defined distances between the LED and each sensor.

Going back to FIG. 1, in the illustrated exemplary embodiment, probe 1102 is shown as comprising two detectors 1108 with a single LED infrared light source 1106, placed on or affixed to a mounting platform or casing 1110 that holds them in place on the forehead in proximity to the frontal cortex when the user is wearing headband 1104. While in this exemplary embodiment, a headband is used, the skilled technician will understand that other designs may be used, for example that include smaller patches that can be affixed with medical adhesive or through suction cups. Moreover, other body areas may be targeted with different means of affixing probe 1102 thereto, without limitation.

In addition to probe 1102, platform or casing 1110 of FIG. 1 further contains the electronics and energy source necessary to power and control probe 1102 and communicate to an external computer. For example, this may include a digital processor 1112 communicatively connected to an internal memory 1114, a power source 1116 and a communication device 1118.

Digital processor 1112 may be any type of digital processor known in the art. This may include low-powered microcontrollers, embedded processors or the like. Generally, digital processor 1112 is communicatively linked to probe 1102 so as to at least control its operation and sometimes additionally process, at least in part, the acquired data. Digital processor 1112 is also communicatively linked to internal memory 1114 which may contain for example instructions for use thereby. Internal memory 1114 can be any form of electronic storage known in the art, or a combination thereof, including read-only memory, random-access memory, or flash memory, to name a few examples. Power source 1116 may comprise one or more rechargeable or non-rechargeable batteries. Communication device 1118 may be any device operable to transmit data to another electronic device. This may include a network adapter for transmitting data over a wired (i.e. ethernet) or wireless connection (i.e. Bluetooth or Wi-Fi). It may also include RF emitters/transmitters, for example a wireless UART RF module or similar. In the illustrated embodiment of FIG. 1, communication device 1108 is shown transmitting data via a wireless signal 1120 to a remote processing device 1122. The skilled technician will understand that other electronic components may also be integrated on headband 102 as required. These may include for example DC/DC converters, or any electronic component required to optimize the functioning of the components already discussed above, without limitation.

In some embodiments, probe 1102 and its associated electronic components may be operable to function in an offline mode in which case the data is stored on board in internal memory 1114 for future download once the wireless link is made available. The device may also function in an online mode when the wireless connection to remote device 1122 is available and can allow real-time download of the data acquired for monitoring and processing purposes.

In some embodiments, remote device 1122 may be any type of a computer with a digital display screen, tablet, smartwatch, smartphone or like general computing device. It generally comprises its own communication device 1124 configured so as to communicate with communication device 1108, an internal memory 1126, a digital processor 1128, some type of display 130 and one or more input devices 1132 (i.e. keyboard, mouse, touch screen, etc.). In some embodiments, remote device 1122 may be operable to receive spectral data acquired by probe 1102 and to process it.

In some embodiments, as remote device 1122 may not have the constraint otherwise imposed on a wearable probe such as that provided by headband 1104, digital processor 1128 may be more powerful than digital processor 1112 on headband 1104, and may thus be relied on to provide more demanding tasks such as data analysis or the like. In other embodiments, if remote device 1122 is also lightweight (smartwatch, etc.), processing may be offloaded, at least in part, to a remote server or similar (not shown) to which remote device 1122 is or can be remotely connected.

Figure 12:
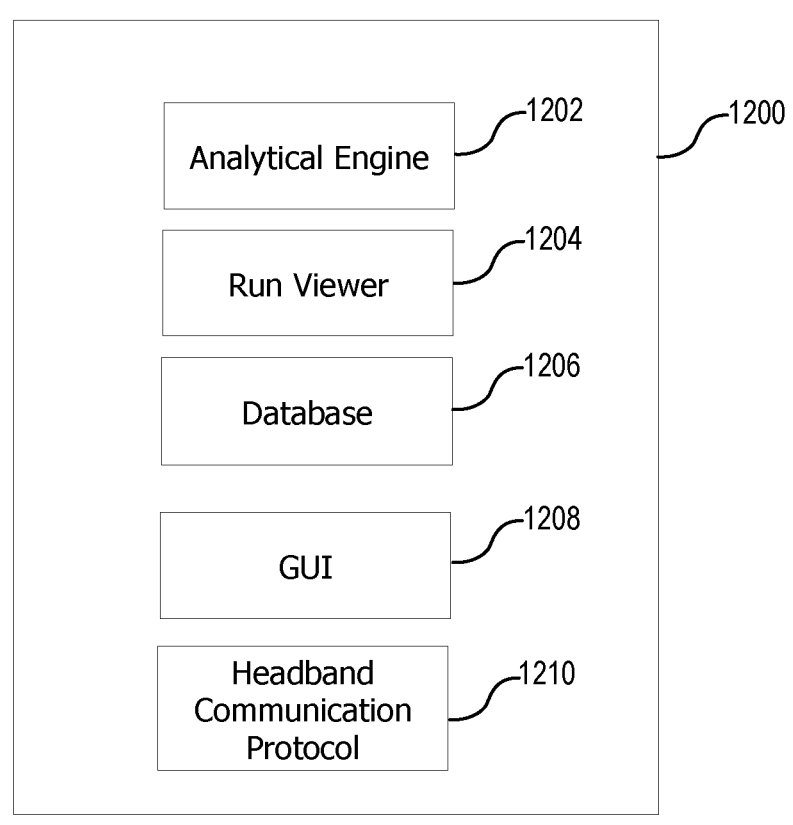
FIG. 12 is a schematic diagram of an exemplary software processing system, in accordance with one embodiment.

With reference to FIG. 12, and in accordance with different embodiments, a software processing system or engine for processing spectral data, generally referred to using the numeral 1200, is discussed. In this exemplary embodiment, processing system 1200 may be executed on remote device 1122, which is in direct communication with the electronics on headband 1102 as mentioned above. More generally, in some embodiments, processing system 1200 may be in the form of a software interface or application interface running or being executed on a computer with a digital display screen, tablet, smartphone application or like general computing device, or again a dedicated device having a graphical or like general computing device.

In some embodiments, processing system 1200 may comprise one or more software modules or features, including for example an analytical engine 1202, a run viewer 1204, a database 1206, a graphical user interface (GUI) 1208 and/or a headband communication protocol interface 1210.

In some embodiments, analytical engine module 1202 comprises software configured or programmed to process spectral data acquired by probe 1102. This may include fitting the spectral data with one or more spectral functions so as to determine the spectral contributions from one or more chromophores or molecules. It may also include using the identified spectral contributions from each chromophore (and thus a related chromophore concentration) to derive one or more related physiological or health-related parameters. These may include, without limitation, blood volume, blood flow rate, breathing rate, heart rate, and blood pressure and/or any medical condition related to a change thereof. In some cases, this may be done using pre-defined analytical models. In other cases, machine-learning or artificial intelligence (AI) algorithms may be used to derive correlations between these one or more physiological parameters and said spectral contributions. Moreover, by combining an analytical model with the high-resolution spectral data acquired by probe 1102, absolute measurements are possible, in contrast with known methods which rely on relative measurements.

In some embodiments, run viewer module 1204 is a program operable to monitor spectral data acquired via probe 1102, in some cases in real-time. This may include generating plots or graphical representations of said spectral data. In some embodiments, module 1204 may further be used to remotely program or configure probe 1102 or any parameter related to the spectral acquisition process (i.e. acquisition frequency, brightness of light source 1106, etc.).

In some embodiments, database module 1206 may include a database software, or a database-interfacing program operable to interface with a remote server-based database. It may be used to store spectral data acquired via probe 1102 but also any processing done thereto via analytical engine 1202. In some embodiments, previous measurements may be stored in database 1206 so as to construct a baseline for one or more physiological or health-related parameters.

In some embodiments, processing system 1200 may include a headband communication protocol interface module 1210. This may include any software used to configure or control data transmission between probe 1102 and remote device 1122 (or to any other computing device), so for example to configure either one of communication devices 1118 or 1124. In some embodiments, this may also include configuring how other parameters related to the functioning of any components located on headband 1104 may also be transmitted. For example, this may include the remaining charge of power source 1116 or any error messages related to malfunctioning hardware components.

In some embodiments, processing system 1200 may further comprise a GUI 1210, displayed for example via display 130, and which may be used to interact with any one of modules 1202 to 1208 via a mouse of touchscreen. In some embodiments, multiple modules may be interacted with simultaneously via GUI 1208.

Figure 13:
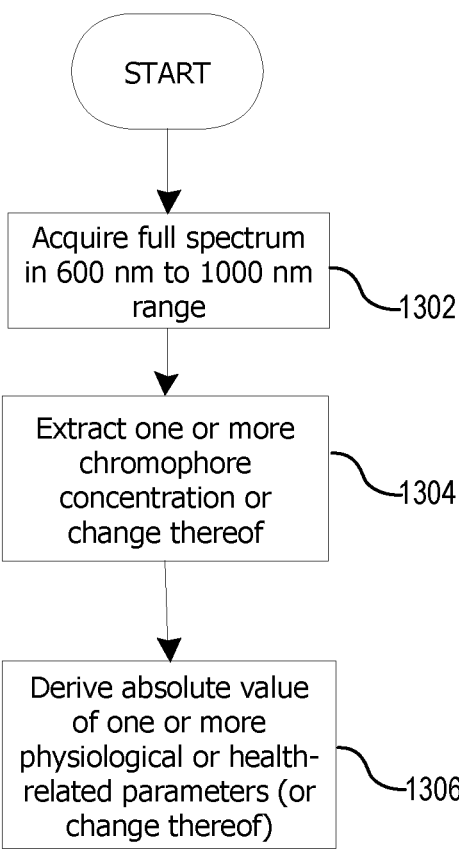
FIG. 13 is a process flow diagram illustrating a monitoring method for assessing certain physiological parameters using the system of FIG. 1, in accordance with some embodiments.

With reference to FIG. 13, and in accordance with one embodiment, a process for monitoring for one or more health-related parameters with system 1100, generally referred to using the numeral 1300, will now be described.

Initially, at step 1302, a full or broad spectrum of the user or patient is acquired via probe 1102. As mentioned above, the exemplary system 1100 is designed so as to acquire a full spectrum between 600 nm and 1000 nm. Different resolutions may be used, for example and without limitation, a resolution of 5 nm from 600 nm to 1000 nm, or 81 wavelengths in total.

At step 1304, the acquired spectral signal or data is analyzed or processed. In some embodiments, it may be preferable to directly send or transmit the acquired raw spectral data to remote device 1122 for analysis (for example to minimize the power requirements of wearable digital processor 1112). In other embodiments, the analysis, processing or pre-processing (i.e. averaging of multiple acquisitions or other) of the acquired spectra may be done, at least in part, via digital processor 1112 located on headband 1104 before being transmitted.

As mentioned above, the high spectral resolution provided by system 1100 provides a higher discrimination ability between various chromophores being monitored. These may include, without limitation, extracting concentrations for chromophores like carbon monoxide, cytochrome oxidase, oxyhemoglobin, deoxyhemoglobin, or other hemoglobin types, melanin, etc. Blood volume changes can also be monitored, for example, where monitored concentrations remain relatively constant but a greater or lesser volume of probed molecules travel across the sensor's field of view over time.

The high resolution and the large range of the acquired spectrum allows, for example, spectral unmixing analysis, wherein the spectral signature can be broken down into its constituent spectral components and the relative proportion of each of these component spectra can be deduced. This has the unique capability of being able to extract known absorption spectra from the at-sensor spectra and find "residual" signatures with spectra of unknown origin. Conversely, a spectral signature can be extracted based only on its unique feature distribution over the entire IR range. This allows better estimates of the material causing that signature. It also allows extraction of spectra with very broad features more accurately, which is not readily available using only a few token wavelengths in a conventional oximeter, since these broad spectra features are more affected by confounding factors. Thus, each spectral component can be resolved or identified. In combination with an analytical model, this allows the calculation of absolute values. This is in contrast with current cerebral oximetry techniques which rely on the calculation of indices (regional saturation, etc.) based on ratios and these can only be relative to baseline measurements. This means that values from one patient to another may vary significantly and comparisons are therefore not easily done.

Different functions or functional forms may be used or fitted to the spectral data to extract distinct chromophore signatures therein. This may include different multivariate analysis methods known in the art for addressing the presence of two or more chromophore components having overlapping spectral features.

Moreover, while conventional cerebral oximeters tend to average readings or measurements over a period of several seconds to be able to output a steady reading, in contrast, system 1100 may be operable, in some embodiments, to deconvolve the physiological parameters for each spectral reading acquired at a high frequency in order to remove any confounding effect and thus be able to render a high-frequency reading of all parameters, which avoids the need to overly average readings to remove those confounding effects.

The nature of spectroximetry, or hyperspectral oximetry, as in the case of system 1100, allows measurement of absolute transmission of energy. Therefore, intra-patient and/or inter-patient measurements can be readily taken, for example, without significant pre-calibration efforts or techniques.

Once one or more chromophore absorption levels have been extracted from the spectral data, in step 1306, these may be correlated with one or more physiological or health-related parameters, or with a change thereof. In some embodiments, the higher level of spectral information acquired by system 1100 may allow to derive correlations with known clinical data using one or more optimization algorithms, for example using AI models or similar (including neural network models or deep-learning models).

Moreover, since the acquired spectral data covers a large band of wavelengths, this allows not only to compare spectra between users or patients, but it also allows customization of the diagnostic value or device response to the target individual.

These one or more physiological or health-related parameters may include, without limitation, blood pressure, blood or tissue oxygenation, pulse, blood flow rate, blood loss or hemorrhaging, cognitive assessments, lung efficiency, rate of O2 consumption by the brain or other physiological system being probed, stress detection, blackout warnings, CPR monitoring, assessment of vital signs, detection of strokes, etc. Some of these will be discussed further below. Moreover, since system 1100 is operable to acquire high-frequency spectral data which contains the presence of multiple chromophore signatures simultaneously, it may thus allow for a perfect synchronization of correlations between the one or more physiological or health-related parameters derived therefrom.

In some embodiments, the absolute nature of the absorption spectra acquired by probe 1102 may allow to detect blood loss, or hemorrhaging. For example, while the SpO2 parameter measured using traditional oximetry techniques only considers the fraction of the hemoglobin molecules in the oxygenated state and not the total hemoglobin content, it cannot provide an absolute reference value from one individual to another. Indeed, it can only provide a measure of the portion of hemoglobin molecules which are/are not oxygenated. In contrast, system 1100 is operable to provide a more complete spectrum and may thus be able to assess the level of hemoglobin concentration from the total absorption of light. In the exemplary case of blood loss, system 1100 may detect the total concentration of hemoglobin going down, even when the oxygen saturation remains at 100%.

In some embodiments, system 1100 may provide diagnostic evaluation via the use of bolus type tests in which an "indicator" (e.g. naturally occurring or foreign tracer molecule or similar) is introduced in the blood and its effects are measured. For example, a patient may receive a shot of high concentration $O_2$, which may be detected via a spike in measured venous oxyhemoglobin, which may be detected in the head or other monitored region. This type of measurement would not be possible with conventional pulse oximetry methods or systems. If the initial amount of $O_2$ introduced is known, system 100 may derive therefrom a concentration of new oxyhemoglobin, which, combined with a measurement of the change in absorption of light in the head (or other region), may be used to derive a venous blood optical "thickness" value. The same process may also be done when monitoring arterial oxyhemoglobin and consequently a corresponding proportion of arterial to venous content in the head can be derived. For instance, if the amount of new arterial oxyhemoglobin resulting from the "shot" is estimated, then changes measured in the oxyhemoglobin absorption can be fitted to a venous volume required to manifest the total spectral absorption observed, thereby providing an indication as to arterial to venous proportions. Other tests may include, but are not limited to, pulmonary efficiency, in that knowing an increase in $O_2$ molecules introduced, one can measure what amount reaching the blood (e.g. via spectral absorption) and qualify or quantify a proportion of the $O_2$ being absorbed into the blood and a speed or efficiency at which it does. These and other similar tests may be done by system 1100 in real-time for each individual.

In some embodiments, the same "bolus" type test may also be used to provide the time of travel between the lungs and a point of interest on the body (e.g. head; extremities such as arms, fingers, feet or legs as a function of blood pressure). This type of measurement may be used to derive a blood flow rate value, for example.

Similarly, since blood flow rate is dependent on blood pressure, similar correlations between flow rates and blood pressure may be derived. Currently, correlations derived using a conventional pulse-oximetry signal and blood pressure are statistically-based and use databases of previously measured signals to optimize an algorithm (such as AI). In contrast, the full Spectrum approach provided by system 100 is more versatile as it is based on direct correlations between different physiological parameters.

In some embodiments, detected changes in oxyhemoglobin and deoxyhemoglobin may be combined with the $O_2$ content being breathed (e.g. the % $O_2$ being breathed), to derive a level of dissolved oxygen in the blood.

In some embodiments, system 1100 may be configured to detect an increase in the optical density related to oxyhemoglobin in the venous blood, and may use the concentration of $O_2$ being breathed (e.g. the % $O_2$ being breathed), to derive a corresponding hemoglobin concentration. This may also be done when measuring a decrease in optical density of oxyhemoglobin with a decreasing concentration of $O_2$ being breathed.

In some embodiments, system 1100 may be used to monitor $O_2$ delivery. For example, in some clinical settings, it may be desirable to administer $O_2$ to a patient to increase the partial pressure of $O_2$ in the patient's lungs and the blood. However, elevated concentrations of $O_2$ in the blood for prolonged time are known to have detrimental effects. Conventional pulse oximeters are not able to show if the patient is in a hyperoxic state (or above partial pressure of 0.21 ATA). In contrast, full spectrum oximetry as provided by system 1100 may be operable to track elevated $O_2$ states. It may also be operable to detect dropping $O_2$ levels before a hypoxic state is even reached, in contrast to a pulse oximeter that would typically only be able to detect the hypoxic state once reached.

In some embodiments, system 1100 may be used in hyperbaric medicine. For example, in some embodiments, system 100 may be configured to track hyperoxic states well above a $O_2$ partial pressure of 0.21 ATA, thus allowing the monitoring of how close the patient is to hazardous levels of oxygen toxicity.

In some embodiments, system 1100 may be used for cognitive assessment during sports or in extreme environments. For example, system 1100 may be configured to provide assessment of oxygenation levels during exercise. It is well known that conventional oximetry does not see or detect increases in blood oxygenation beyond SpO2 of 100%, which is very close to the value anyone has normally at rest. In contrast, system 1100 may be operable to see or detect increases in the level of oxyhemoglobin reaching the organ of interest (e.g. brain) in a specified unit of time during exercise. For instance, this may be used to indicate an increase in blood flow, and thus of oxyhemoglobin, to the organ under observation, which translates in a greater delivery of $O_2$ to that organ. Thus, in some embodiments, system 1100 may be used to monitor or assess the level of increased oxygenation from one activity to another, which may be used to create a baseline by finding normal increases in oxygen delivery to the brain (or other organs) using a sample population. Thus, measurements from an individual may be compared to this baseline and this used to assess performance, impairments, etc.

In some embodiments, system 1100 may be configured to monitor the rate of $O_2$ consumption in the brain or other organ of interest. For example, with normal air, arterial blood is almost 100% saturated. If 100% $O_2$ is breathed, the venous deoxyhemoglobin in the organ will decrease by an amount proportional to the amount of $O_2$ not metabolized by the tissue under study. Thus, by knowing the input quantity or amount of air and knowing what is left over from the dissolved $O_2$ that went back into the venous hemoglobin (thus raising its oxyhemoglobin content), system 1100 may be configured to derive the portion of $O_2$ taken up by the organ of interest. In some embodiments, this may be done on a population sample which may then be used as a reference or baseline for diagnostic of other individuals.

In some embodiments, system 1100 may be operable to derive a lung efficiency value or similar.

By introducing a known increase in $O_2$ content being breathed and measuring the effective change in oxy and deoxy hemoglobin, and if applicable knowing the metabolized amount in the tissue under investigation, system 100 may derive therefrom a measure of efficiency of $O_2$ transfer occurring at the pulmonary level. Conversely, $O_2$ intake may be reduced and system 100 used to monitor the corresponding decrease of oxyhemoglobin optical density in the arteries.

In some embodiments, system 1100 may be operable to derive a concentration of $O_2$ breathed. This may be done as described above for assessing lung efficiency, but here assuming a fixed level of lung efficiency to derive the concentration being breathed. In some embodiments, system 1100 may thus be combined or used in conjunction with a rebreather diving apparatus or similar.

In some embodiments, system 1100 may be used for stress detection and assessment. For example, stress in a user or patient impacts physiological parameters such as pulse, respiration, and blood flow rate. All these parameters may be correlated to the spectra recorded via system 1100. An assessment on the stress level can be made using a combination of known states for each parameter as well as known changes to these parameters (i.e. sudden increase in heart rate and breathing).

In some embodiments, system 1100 may be configured to alert for imminent blackout in an individual or user. The onset of blackout in a user may be predicted based on the oxygenation state of the person. For example, for military pilots, a drop of blood flow to the brain, or a drop in oxygenation levels may be used to mitigate risk of blackouts.

In some embodiments, system 1100 may be used to monitor cardiopulmonary resuscitation (CPR) maneuvers or the like. Currently, CPR is performed using set recommended protocols and procedures for the frequency of chest compressions and mouth-to-mouth assisted breathing. These protocols are established based on experience. Means for an assessment of the performance of CPR given to a patient in real-time while CPR is administered can significantly improve patient outcome. The protocol could be adapted to the patient's needs given specific scenario and response. However, one of the problems with traditional cerebral oximetry is the lack of common baseline from one patient to another. It is also not clear what values given by one instrument should be used as target since (1) the index is relative, (2) indices are not calculated the same way, (3) the same index can vary from one device to the next due to design factors, (4) lack of clinical studies across all devices, (5) variability in readings from one patient to another using the same device given skin type, ethnic background, etc. Another significant disadvantage of traditional cerebral oximetry is the fact that the index typically is calculated using an integration time significantly longer than a normal heartbeat. Sensitivity to minute changes in hemoglobin is therefore compromised. Finally, conventional pulse oximetry will not work when the patient has weak or no pulse.

Full spectrum oximetry as provided by system 1100 may allow for the instantaneous assessment of vital signs. For example, by deconvolving spectral signatures, individual contribution of each type of chromophore may be measured. High-frequency measurements can see variations in blood flow that could be indicative of chest compressions. This approach can also define a target "absolute index" of absorption in the brain caused by oxyhemoglobin, blood flow, and other useful parameters. This index can be then be used for all individuals.

In some embodiments, system 1100 may be configured to detect strokes resulting from the blockage of blood flow to the brain. As discussed above, reduction of blood flow may be derived by system 1100 via a significant reduction in absorption of key spectral indicators.

Figure 14:
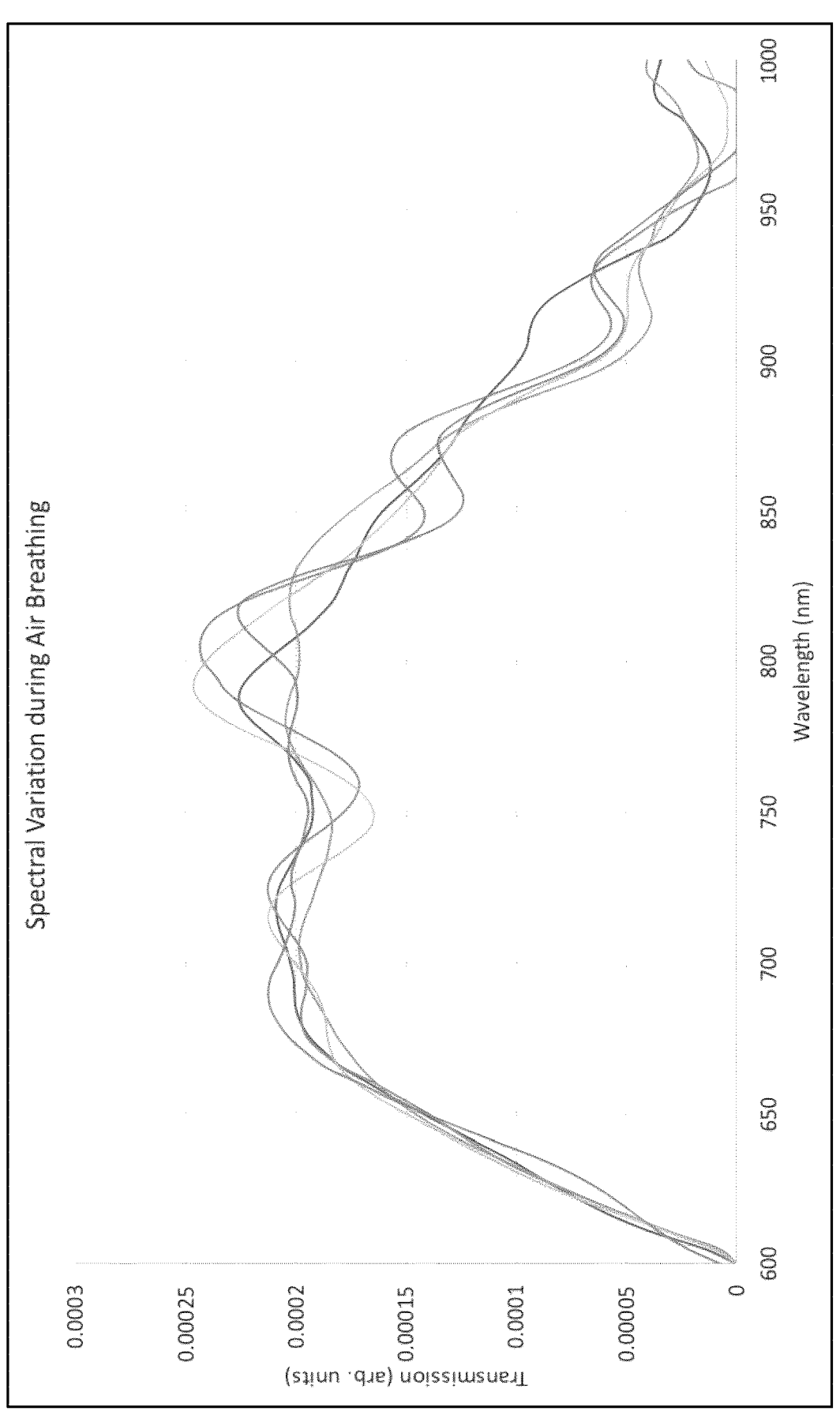
FIG. 14 is an exemplary plot of a spectral variation measured in a user breathing normal air while sitting in a chair, in accordance with one embodiment.
Figure 15:
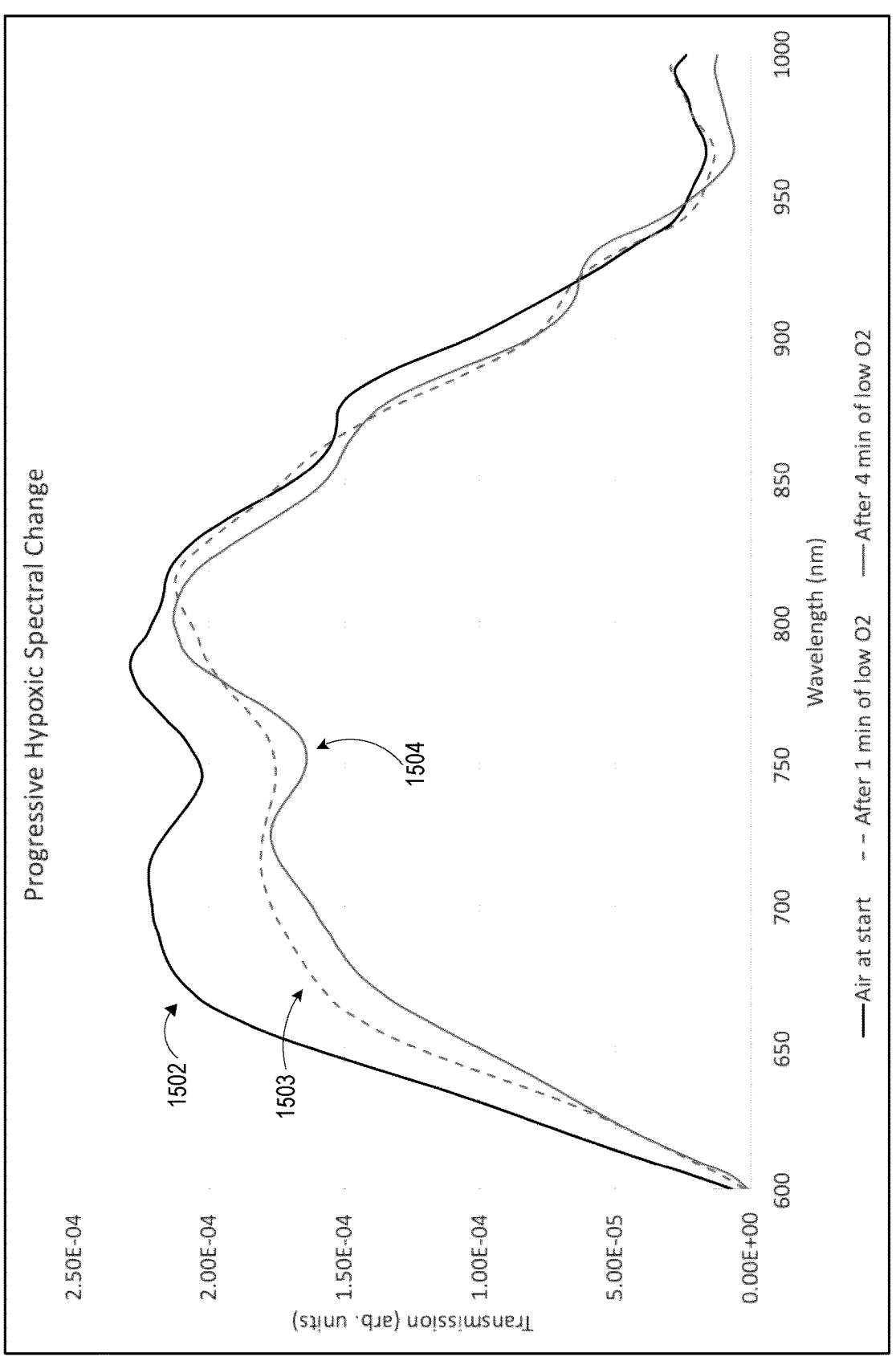
FIG. 15 is an exemplary plot of an average change in recorded spectra when switching from normal air (21% O2) to a hypoxic gas containing 5% O2, in accordance with one embodiment.
Figure 16:
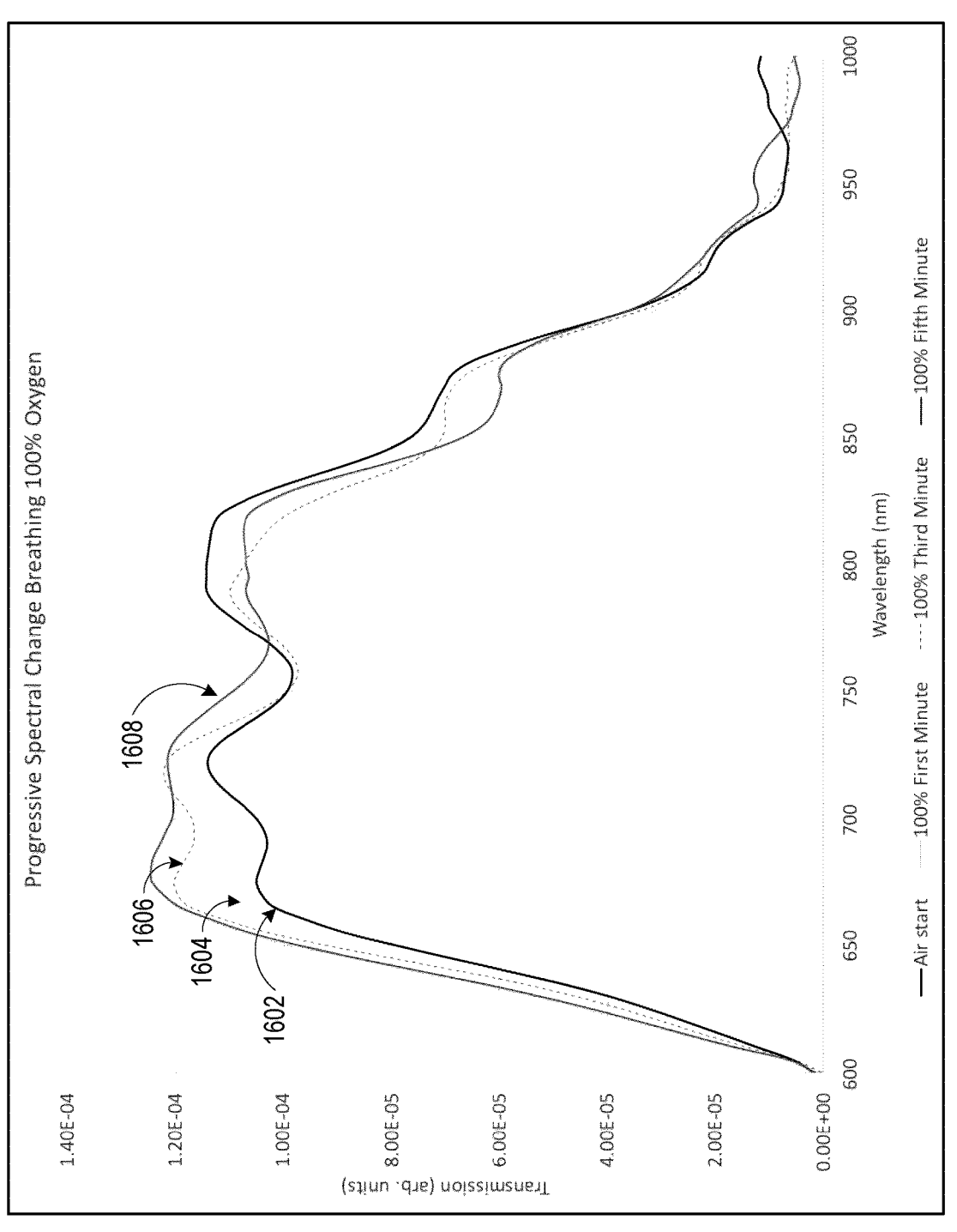
FIG. 16 is an exemplary plot of an average change in recorded spectra when switching from normal air (21% $O_2$) to breathing pure oxygen (100% $O_2$), in accordance with one embodiment.

With reference to FIGS. 14 to 16, and in accordance with one exemplary embodiment, an exemplary set of measurements acquired using an exemplary embodiment of system 1100 will be discussed.

FIG. 14 shows an exemplary plot of multiple spectral transmission curves acquired at the cerebral level for a user wearing system 1100 breathing normal air while being in a seated position. The plot shows randomly acquired spectra over a two-minute period. The time sampling of repeated measurements (i.e. different curves) shows variations that are due to the inherent physiological changes caused by varying blood flow (heart beats, blood pressure, etc.), breathing rate, and other such normal body functions. Spectra taken at various times therefore will show variations in the acquired spectra due to these inherent physiological changes. This allows to derive values for physiological parameters such as pulse, blood flow, head orientation, blood volume, blood pressure, etc. with adequate modeling, since the spectral differences can be used to derive the physiological parameters that affect these readings such as pulse, blood volume, blood volume, blood pressure, etc.

In some embodiments, the transmission curve of normal air at 21% (FIG. 14) can represent a baseline to which changes arising from different O2 concentration can be interpreted.

With reference to FIG. 15, a plot showing an average change of spectral readings when switching from normal air breathing, as seen in the previous FIG. 14, to breathing a hypoxic gas that contains 5% $O_2$ will now be discussed. Breathing a hypoxic gas results in a significant lowering of the level of oxygen reaching the blood and tissues. The plot of FIG. 15 shows the progressive change in spectral readings with line 1502 representing an average of multiple spectra taken during one-minute breathing air in a sitting position as in the previous plot of FIG. 14. Meanwhile, line 1503 shows the average of multiple spectra taken after a minute of breathing the hypoxic mix. Finally, line 1504 is the average of multiple spectra taken after breathing 4 minutes of the hypoxic mix. In this case, there is a clear decrease in the transmission in the 700 nm area which is consistent with an increase in absorption due to elevated deoxyhemoglobin levels.

Similarly, FIG. 16 is a plot showing various acquired spectra when the user switches from breathing normal air (21%) to breathing pure oxygen (100%). Line 1602 shows the average of multiple spectra taken during the first minute of breathing normal air. Lines 1604 and 1606 are the average of multiple spectra acquired during the first and third minutes, respectively. Line 608 is the average of multiple spectra acquired during the fifth minute of breathing pure oxygen. While conventional pulse oximeters, as well as cerebral oximeters would not show significant change in these conditions, the full-spectrometric signals acquired via system 1100 clearly show the progressive change related to the changing breathing conditions.

In light of the above, and accordance with one embodiment, a device for real-time vital sign monitoring for individuals in extreme and/or harsh environments is provided, whereby such environments expose users to anomalous environmental respiratory conditions, as described above. Namely, within this context, extreme environments may include any situation where an individual is experiencing lower or higher ambient pressures or requires delivery of oxygen from an external source. For example, these situations include high altitude pilots and underwater divers.

In one such embodiment, the device can detect and track multiple vital signs including heart rate, breathing rate, temperature, and oxygenation. The device consists of a custom light source and a series of optical detectors that operate in a wide range of frequencies, as further detailed below, for example. Light reaching the detectors at specific frequency ranges is tracked and used to derive the physiological parameters of interest, namely those representative of the user's current and/or cumulative physiological response to exposure to the anomalous environmental respiratory conditions. As further detailed below, in this embodiment, operation of the device's optical physiological sensing and monitoring system differs from conventional oximetry in that the device is not dependent on the detection of a pulse to acquire meaningful data.

In one particular embodiment, measurements are made directly at the cerebral level. Consequently, the device is designed to be worn on the forehead where it can be integrated into existing equipment (mask, hoodie, HUD unit, etc.) or as a standalone patch. The device is not limited to this placement and can be also put elsewhere on the body. Outside the scope of underwater applications, the device can also be used for the monitoring of pilot cognitive performance, for example. The device can generally be used in any scenario requiring real-time continuous physiological monitoring.

As introduced above, the device is operable to track oxygen levels in both hypoxic as well as hyperoxic conditions. For this reason, the device is amenable for underwater environments where divers are exposed to significant dangers due to oxygen toxicity.

There are generally no current devices that can track higher than normal oxygenation levels in a non-invasive and continuous manner. Conventional measurement of oxygenation consists of detecting arterial saturation ($SpO_2$) using a pulse oximeter placed on the extremities of the body (fingers, toes, ear lobes, etc.). In the context of diving, $SpO_2$ is not very useful as it is only indicative of arterial oxyhemoglobin levels, can only be used for hypoxia, and is ineffective in cases of reduced blood circulation such as in cold temperatures.

Comparatively, devices as described herein in accordance with some embodiments, are operable to detect and track hyperoxia resulting from $O_2$ partial pressures well above 0.21 ATA as experienced in diving applications.

Accordingly, the device represents a complete vital sign monitoring solution and allows for a continuous adaptation of a dive profile, for example, to the actual physiological condition of the diver in open, semi-closed, and closed circuit scenarios, while also mitigating the dangers of hyperoxia.

To demonstrate the tracking of oxygen during hyperoxia, the herein-described approaches were tested in real underwater environments and in hyperbaric chambers. As an example, FIG. 8 (described above) shows data acquired during a dive in a hyperbaric chamber. The diver is initially at the surface breathing air. A first descent reaches 30 feet (t=600 sec.). After a few minutes, the diver switches to 100% O2 while the depth is kept unchanged. The diver is then brought up to 15 feet where a switch back to air occurs after a few minutes. For reference, the breathing gas and partial pressure (pO2) at each depth is indicated on the graph. It can be readily observed that the light transmission detected by the device correlates directly to the changes in oxygen experienced by the diver.

Two features can be highlighted in FIG. 8. First is the fact that the device follows the changes in oxygen levels actually experienced by the diver at a physiological level and not through any derivation based on depth and gas mix. For example, when the first switch from air to 100% occurs, the transmission levels are instantly reduced (indicating increased oxygen) while the atmospheric pressure remains that of 30 feet depth.

Secondly, the device provides a means to track and mitigate long term exposure to $O_2$. This is demonstrated by comparing the first period in which the diver is breathing air at 30 feet pressure and the last period where the diver is breathing air at 15 feet pressure. Based only on depth and gas mix, it would be expected that the level of oxygen exposure in the diver's system is less in the latter period at 15 feet than in the initial period at 30 feet. The acquired data however shows slightly increased levels of $O_2$ exposure at 15 feet. The cause of this is explained by residual $O_2$ in the diver's system resulting from high exposure while breathing 100% $O_2$. To our knowledge this figure is the first such recorded evidence demonstrating that partial pressure based on gas mix and depth alone is not sufficient to assess a diver's true exposure to oxygen and risks of oxygen toxicity.

Using this approach, the device is capable of monitoring all vital signs in real-time during a dive and allow for a continuous adaptation of the dive profile to the actual physiological condition of the diver. For example, the diver's real-time physiological data can feedback into the rebreather or dive computer to continuously adapt the dive to the actual physiological state of the diver, independently of the sensors onboard the rebreather.

Tests were conducted to demonstrate the impact of the level of physical activity on oxygen exposure and its associated risks in hyperoxic conditions. For example, FIG. 9 (described above) shows the synchronous tracking of oxygenation, heart rate, and breathing rate as the diver increases the level of physical exertion. The diver descended to 57 feet and performed intense physical activity without altering depth or breathing gas. Shortly after the onset of the physical activity, both the heart rate (middle curve) and the breathing rate (bottom curve) increased sharply. This led to a detectable increase in oxygenation shown by the decrease in light transmission (to curve). The increase in oxygenation is steady and continuous throughout the period of intense activity.

This data suggests the importance of accounting for physiological parameters in the assessment of oxygen exposure and risks of oxygen toxicity.

Accordingly, a computational process as described herein that can take physiological parameters into account can compensate for the variability of a diver's reaction to the same dive conditions at different times. Actionable decisions can then be tailored to the diver's specific condition at a given time. Actionable decisions can include but are not limited to: surface, reduce depth, or allow increased depth; prolong or reduce dive time, alter gas mix; reduce physical activity; etc.

This device allows the significant improvement adding physiological parameters to the current approaches for dive management that are otherwise solely based on environmental conditions (pressure, running time, etc.). Whereas existing algorithms make assumptions based on theoretical models of the physiological reactions to environmental conditions, this approach allows new algorithms that take into account the actual physiological parameters as they are being measured in real-time while the diver is exposed to environmental stresses.

Several advantages to real-time physiology-adapted dive management may thus include, but are not limited to, any combination of: Enhanced prediction of hazardous health states; Optimal physical performance; Ability to train Machine-Learning algorithms (Artificial Intelligence) to tailor predictions to individual divers; Unique customized adapted profiles based on day-to-day conditions; Tracking of performance enhancement over time; Detection of anomalies based on history of physiological response; Objective comparison between diver performances; Etc.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become apparent to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims. Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the disclosure.

What is claimed is:

1. An system for monitoring a user exposed to an anomalous environmental respiratory condition during an anomalous respiratory environment experience cycle having a maximum exposure risk defined therefor, the system comprising:

an environmental sensor operable to monitor a respiratory environment parameter representative of the anomalous environmental respiratory condition that defines the experience cycle;

a physiological sensor operable to concurrently monitor a physiological parameter representative of the user's cumulative physiological response to the anomalous environmental respiratory condition over time during the experience cycle; and a digital data processor having stored in association therewith operable to monitor said physiological parameter against a user-agnostic exposure risk profile designated to avoid exceeding the maximum exposure risk for a generic user exposed to the experience cycle based on an anticipated condition of the generic user as a function of a cumulative exposure during the experience cycle, wherein said digital data processor is operable to monitor said physiological parameter against said user-agnostic exposure risk profile and identify therefrom an adapted user-specific exposure risk profile that deviates from said user-agnostic exposure risk profile to automatically output an adaptive exposure risk indicator in accordance with said adapted user-specific exposure risk profile that adaptively guides customization of the experience cycle while adhering to the maximum exposure risk;

wherein said digital data processor automatically evaluates a user's current condition based on said physiological parameter;

upon said current condition being automatically evaluated as substantially worse than the anticipated condition for a current cumulative exposure, automatically adapts said user-specific exposure risk profile to reflect an increased user-specific cumulative exposure risk for the user and thereby reduce an overall acceptable cumulative exposure setting associated with the experience cycle;

upon said current condition being automatically evaluated as substantially better than the anticipated condition for a current cumulative exposure, automatically adapts said user-specific exposure risk profile to reflect a reduced user-specific cumulative exposure risk for the user and thereby increase an overall acceptable cumulative exposure setting associated with the experience cycle.

2. The system of claim 1, wherein said digital data processor is operable to adaptively compute said user-agnostic exposure risk profile over time based on said respiratory environment parameter.

3. The system of claim 1, wherein said adaptive exposure risk indicator comprises an adaptive maximum experience duration value, wherein said adaptive maximum experience duration value is set for a given or a maximum depth.

4. The system of claim 1, wherein the experience comprises a hypobaric experience, and wherein said respiratory environment parameter comprises a current high altitude value and an exposure duration for said current high altitude.

5. The system of claim 1, wherein the experience comprises a hyperbaric experience, and wherein said respiratory environment parameter comprises a current depth and an exposure duration for said depth.

6. The system of claim 1, wherein said physiological parameter comprises at least one of a blood oxygen value or a tissue oxygen value.

7. The system of claim 1, wherein said physiological parameter comprises an absolute concentration of at least one of deoxyhemoglobin, oxyhemoglobin or dissolved oxygen.

8. The system of claim 1, wherein said physiological parameter comprises at least three of carbon monoxide, melanin, cytochrome oxidase, oxyhemoglobin, or deoxyhemoglobin.

9. The system of claim 1, wherein said physiological parameter comprises at least one of a blood inert gas value or a tissue inert gas value.

10. The system of claim 1, wherein said digital data processor is further operable to automatically evaluate said adapted user-specific exposure risk profile over multiple exposure cycles to predictively output subsequent adapted user-specific exposure risk profiles, wherein each said adapted user-specific exposure risk profile is digitally evaluated to update a user-specific physiological response model representative of the user's anticipated response to said multiple exposure cycles, and wherein said user-agnostic exposure risk profile is automatically adapted for a subsequent exposure cycle as a function of said user-specific physiological response model.

11. The system of claim 1, wherein said physiological sensor comprise an infrared or near-infrared probe, wherein said physiological sensor comprises a broad spectrum oximeter.

12. A computer-implemented method, implemented by one or more digital processors, for monitoring a user exposed to an anomalous environmental respiratory condition during an anomalous respiratory environment experience cycle having a maximum exposure risk defined therefor, the method comprising:

receiving as input, via an environmental sensor, a respiratory environment parameter representative of the anomalous environmental respiratory condition that defines the experience cycle;

concurrently receiving as input, via a physiological sensor, a physiological parameter representative of the user's cumulative physiological response to the anomalous environmental respiratory condition over time during the experience cycle; and digitally monitoring said physiological parameter against a stored user-agnostic exposure risk profile designated to avoid exceeding the maximum exposure risk for a generic user exposed to the experience cycle based on an anticipated condition of the generic user as a function of a cumulative exposure during the experience cycle, and identifying therefrom an adapted user-specific exposure risk profile that deviates from said user-agnostic exposure risk profile; and automatically outputting an adaptive exposure risk indicator in accordance with said adapted user-specific exposure risk profile that adaptively guides customization of the experience cycle while adhering to the maximum exposure risk, wherein said user-agnostic exposure risk profile is adaptively computed over time based on said respiratory environment parameter;

wherein said monitoring and identifying comprises automatically evaluating a user's current condition based on said physiological parameter;

upon said current condition being automatically evaluated as substantially worse than an anticipated condition for a current cumulative exposure, automatically adapting said user-specific exposure risk profile to reflect an increased user-specific cumulative exposure risk for the user and thereby reduce an overall acceptable cumulative exposure setting associated with the experience cycle; and upon said current condition being automatically evaluated as substantially better than an anticipated condition for a current cumulative exposure, automatically adapting said user-specific exposure risk profile to reflect a reduced user-specific cumulative exposure risk for the user and thereby increase an overall acceptable cumulative exposure setting associated with the experience cycle.

13. The computer-implemented method of claim 12, wherein said adaptive exposure risk indicator comprises an adaptive maximum experience duration value, wherein said adaptive maximum experience duration value is set for a given or a maximum depth.

14. The computer-implemented method of claim 12, wherein the experience comprises a hypobaric experience, and wherein said respiratory environment parameter comprises a current high altitude value and an exposure duration for said current high altitude.

15. The computer-implemented method of claim 12, wherein the experience comprises a hyperbaric experience, and wherein said respiratory environment parameter comprises a current depth and an exposure duration for said depth.

16. The computer-implemented method of claim 12, further comprising automatically evaluating said adapted user-specific exposure risk profile over multiple exposure cycles to predictively output subsequent adapted user-specific exposure risk profiles, wherein each said adapted user-specific exposure risk profile is digitally evaluated to update a user-specific physiological response model representative of the user's anticipated response to said multiple exposure cycles, and wherein said user-agnostic exposure risk profile is automatically adapted for a subsequent exposure cycle as a function of said user-specific physiological response model.

17. A non-transitory computer-readable medium comprising digital instructions for implementation by one or more digital processors for monitoring a user exposed to an anomalous environmental respiratory condition during an anomalous respiratory environment experience cycle having a maximum exposure risk defined therefor, by:

accessing a respiratory environment parameter representative of the anomalous environmental respiratory condition that defines the experience cycle;

concurrently accessing a physiological parameter representative of the user's cumulative physiological response to the anomalous environmental respiratory condition over time during the experience cycle; and digitally monitoring said physiological parameter against a stored user-agnostic exposure risk profile designated to avoid exceeding the maximum exposure risk for a generic user exposed to the experience cycle based on an anticipated condition of the generic user as a function of a cumulative exposure during the experience cycle, and identifying therefrom an adapted user-specific exposure risk profile that deviates from said user-agnostic exposure risk profile; and automatically outputting an adaptive exposure risk indicator in accordance with said adapted user-specific exposure risk profile that adaptively guides customization of the experience cycle while adhering to the maximum exposure risk, wherein said user-agnostic exposure risk profile is adaptively computed over time based on said respiratory environment parameter;

wherein said monitoring and identifying comprises automatically evaluating a user's current condition based on said physiological parameter;

upon said current condition being automatically evaluated as substantially worse than an anticipated condition for a current cumulative exposure, automatically adapting said user-specific exposure risk profile to reflect an increased user-specific cumulative exposure risk for the user and thereby reduce an overall acceptable cumulative exposure setting associated with the experience cycle; and upon said current condition being automatically evaluated as substantially better than an anticipated condition for a current cumulative exposure, automatically adapting said user-specific exposure risk profile to reflect a reduced user-specific cumulative exposure risk for the user and thereby increase an overall acceptable cumulative exposure setting associated with the experience cycle.

18. The non-transitory computer-readable medium of claim 17, wherein said adaptive exposure risk indicator comprises an adaptive maximum experience duration value, wherein said adaptive maximum experience duration value is set for a given or a maximum depth.

19. The non-transitory computer-readable medium of claim 17, wherein the experience comprises a hypobaric experience, and wherein said respiratory environment parameter comprises a current high altitude value and an exposure duration for said current high altitude.

20. The non-transitory computer-readable medium of claim 17, wherein the experience comprises a hyperbaric experience, and wherein said respiratory environment parameter comprises a current depth and an exposure duration for said depth.

21. The non-transitory computer-readable medium of claim 17, further comprising automatically evaluating said adapted user-specific exposure risk profile over multiple exposure cycles to predictively output subsequent adapted user-specific exposure risk profiles, wherein each said adapted user-specific exposure risk profile is digitally evaluated to update a user-specific physiological response model representative of the user's anticipated response to said multiple exposure cycles, and wherein said user-agnostic exposure risk profile is automatically adapted for a subsequent exposure cycle as a function of said user-specific physiological response model.

* * * * *